US010597699B2

(12) United States Patent
Moll

(10) Patent No.: US 10,597,699 B2
(45) Date of Patent: Mar. 24, 2020

(54) COPY NUMBER PRESERVING RNA ANALYSIS METHOD

(71) Applicant: LEXOGEN GMBH, Vienna (AT)

(72) Inventor: Pamela Moll, Vienna (AT)

(73) Assignee: LEXOGEN GMBH, Vienna (AT)

( * ) Notice: Subject to any disclaimer, the term of this patent is extended or adjusted under 35 U.S.C. 154(b) by 161 days.

(21) Appl. No.: 15/127,672

(22) PCT Filed: Mar. 20, 2015

(86) PCT No.: PCT/EP2015/055961
§ 371 (c)(1),
(2) Date: Sep. 20, 2016

(87) PCT Pub. No.: WO2015/140307
PCT Pub. Date: Sep. 24, 2015

(65) Prior Publication Data
US 2018/0171384 A1 Jun. 21, 2018

(30) Foreign Application Priority Data
Mar. 21, 2014 (EP) ..................................... 14161135

(51) Int. Cl.
C12Q 1/6806 (2018.01)
C12Q 1/6851 (2018.01)
(Continued)

(52) U.S. Cl.
CPC ....... C12Q 1/6806 (2013.01); C12N 15/1096 (2013.01); C12Q 1/686 (2013.01);
(Continued)

(58) Field of Classification Search
None
See application file for complete search history.

(56) References Cited

U.S. PATENT DOCUMENTS 6,406,891 B1 6/2002 Legerski
2004/0033499 A1 2/2004 Ilsley
(Continued)

FOREIGN PATENT DOCUMENTS

CN 102016070 A 4/2011
CN 102533752 A 7/2012
(Continued)

OTHER PUBLICATIONS

Bodescot et al., "Efficient Second-Strand cDNA Synthesis Using T7 DNA Polymerase," DNA and Cell Biology, vol. 13, No. 9, pp. 977-985. (Year: 1994).*
(Continued)

Primary Examiner — Young J Kim
(74) Attorney, Agent, or Firm — Wolf, Greenfield & Sacks, P.C.

(57) ABSTRACT

The present invention provides a method for generating an amplified nucleic acid portion of a template RNA molecule, comprising after having obtained a template RNA, annealing a first oligonucleotide primer at a preselected 3' terminal nucleic acid region of the template RNA, elongating the first oligonucleotide primer in a template specific manner thereby obtaining a first elongated strand, removing the RNA template, annealing one or more further oligonucleotide primers to the first elongated strand, elongating the one or more further oligonucleotide primers in a template specific manner without strand displacement of polynucleotides annealed to the first elongated strand or using a polymerase that destroys a displaced strand, thereby generating further elongation products, isolating and/or amplifying an elongation product of said further elongation product comprising a nucleic acid portion that is elongated complementary to the first oligonucleotide primer; as well as kits for performing the method.

29 Claims, 7 Drawing Sheets

Figure 1:
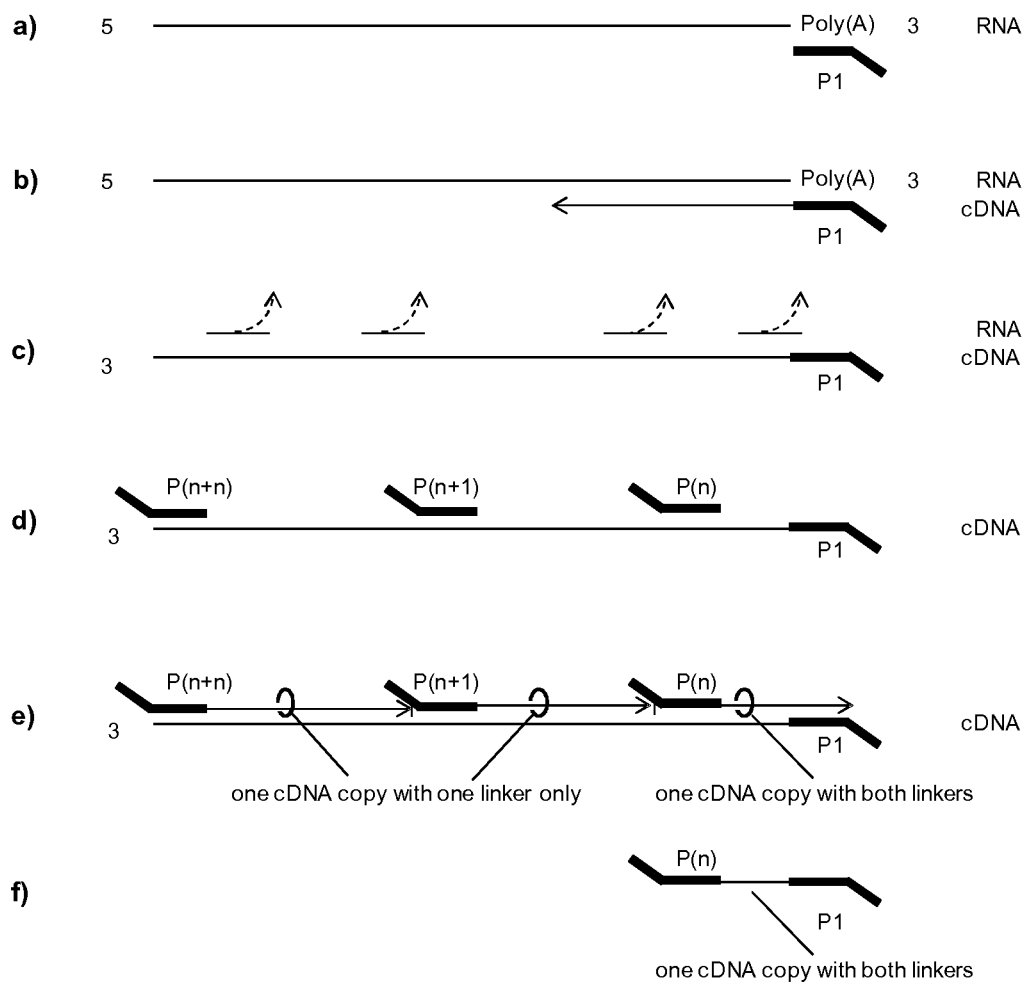

Specification includes a Sequence Listing.

(51) Int. Cl.
*C12Q 1/6853* (2018.01)
*C12Q 1/686* (2018.01)
*C12N 15/10* (2006.01)
*C40B 20/04* (2006.01)

(52) U.S. Cl.
CPC ......... *C12Q 1/6851* (2013.01); *C12Q 1/6853* (2013.01); *C40B 20/04* (2013.01); *C12Q 2521/101* (2013.01); *C12Q 2521/107* (2013.01); *C12Q 2521/327* (2013.01); *C12Q 2525/155* (2013.01); *C12Q 2525/173* (2013.01); *C12Q 2525/179* (2013.01)

(56) References Cited

U.S. PATENT DOCUMENTS

| | | | |
|---|---|---|---|
| 2009/0239232 A1* | 9/2009 | Kurn | C12N 15/1096 435/6.11 |
| 2010/0035249 A1* | 2/2010 | Hayashizaki | C12Q 1/6809 435/6.14 |

FOREIGN PATENT DOCUMENTS

| | | |
|---|---|---|
| CN | 102534813 A | 7/2012 |
| CN | 102817085 A | 12/2012 |
| EP | 1 371 726 A1 | 12/2003 |
| JP | 2012-506246 | 3/2012 |
| WO | WO 2002/045472 A2 | 6/2002 |
| WO | WO 2007/103018 A2 | 9/2007 |
| WO | WO 2009/103027 A2 | 8/2009 |
| WO | WO 2010/046441 A1 | 4/2010 |
| WO | WO 2010/131645 | 11/2010 |
| WO | WO 2013/038010 A2 | 3/2013 |

OTHER PUBLICATIONS

Bodescot et al., Efficient second-strand cDNA synthesis using T7 DNA polymerase. DNA Cell Biol. Sep. 1994;13(9):977-85.

Costa et al., Uncovering the complexity of transcriptomes with RNA-Seq. J Biomed Biotechnol. 2010;2010:853916. doi: 10.1155/2010/853916. Epub Jun. 27, 2010. Review.

Deangelis et al., Solid-phase reversible immobilization for the isolation of PCR products. Nucleic Acids Res. Nov. 25, 1995;23(22):4742-3.

Derti et al., A quantitative atlas of polyadenylation in five mammals. Genome Res. Jun. 2012;22(6):1173-83. doi: 10.1101/gr.132563.111. Epub Mar. 27, 2012.

Fox-Walsh et al., A multiplex RNA-seq strategy to profile poly(a+) RNA: application to analysis of transcription response and 3' end formation. Genomics. Oct. 2011;98(4):266-71. doi: 10.1016/j.ygeno.2011.04.003. Epub Apr. 15, 2011.

Hooper et al., Estimating DNA coverage and abundance in metagenomes using a gamma approximation. Bioinformatics. Feb. 1, 2010;26(3):295-301. doi: 10.1093/bioinformatics/btp687. Epub Dec. 14, 2009.

Hoque et al., Analysis of alternative cleavage and polyadenylation by 3' region extraction and deep sequencing. Nat Methods. Feb. 2013;10(2):133-9. doi: 10.1038/nmeth.2288. Epub Dec. 16, 2012.

Shepard et al., Complex and dynamic landscape of RNA polyadenylation revealed by PAS-Seq. RNA. Apr. 2011;17(4):761-72. doi: 10.1261/rna.2581711. Epub Feb. 22, 2011.

Wendl et al., The theory of discovering rare variants via DNA sequencing. BMC Genomics. Oct. 20, 2009;10:485. doi: 10.1186/1471-2164-10-485.

Wilkening et al., An efficient method for genome-wide polyadenylation site mapping and RNA quantification. Nucleic Acids Res. Mar. 1, 2013;41(5):e65. doi: 10.1093/nar/gks1249. Epub Jan. 7, 2013. Erratum in: Nucleic Acids Res. Jul. 2013;41(12):6370.

Kawasaki, PCR Protocols: A Guide to Methods and Applications. Chapter 3: Amplification of RNA. Edited by M. A. Inns, D. H. Gelfand, J. J. Sninsky and T. J. White. Academic Press, London. 1$^{st}$ Edition, Dec. 12, 1991:21-27.

[No Author Listed] User Guide: Superscript ® Choice system for cDNA synthesis. Jan. 18, 2013. Retrieved from https://assets.thermofisher.com/TFS-Assets/LSG/manuals/superscript_choice_man.pdf. On Oct. 25, 2018.

Lin et al., Construction of cDNA library of suckling mouse osteoblasts using yeast two-hybrid system. Chinese J Osteoporosis. 19(9);Sep. 30, 2013:930-933.

* cited by examiner

| SEQ ID: | Sequence | nt | Type |
|---|---|---|---|
| 1 | A*C*T*GTAAAACGACGGCCAGTATAGTTC GCTCGGTGACCCTGGTCTTTCTGGTGCTTG TCTCACTGACCGGCCTGTATGCTATCCAGA GTGAGTGCCTCTTGTCAAGAACATATAGAT AGGCTCCGTTGCTAATCTGAAGGTCGAA | 145 | DNA |
| 2 | G*T*C*CAGCTACCTAGGTCATGTACTACG GAGCCTATCTATATGTTCTTGACA | 51 | DNA |
| 3 | /5Phos/CAGTGAGACAAGCACCAGAAAGACCAGGGT CA*C*C*G | 35 | DNA |
| 4 | CAGTGAGACAAGCACCAGAAAGACCAGGGT CA*C*C*GAGCGAACTATACTGGCCGTCGTTTTACAGT | 65 | RNA |
| 5 | G*T*C*CAGCTACCTAGGTCATGTACTACGGAG CCTATCTATATGTTCTTGACAAGAGGCACT CACTCTGGATAGCATACAGGCCGGT | 85 | DNA |
| 6 | G*T*C*CAGCTACCTAGGTCATGTACTACGGAG CCTATCTATATGTTCTTGACAAGAGGCACT CACTCTGGATAGCATACAGGCCGGTCAGTG AGACAAGCACCAGAAAGACCAGGGTCACCG AGCGAACTATACTGGCCGTCGTTTTACAGT | 150 | DNA |
| 7 | GTTGTCACCAGCATCCCTAGACCCGTACAG TGCCCACTCCCCTTCCCAGTTTCCGACTGT CCCCGGCCTCCTGCGGCCCATTCC AAAAAAAAAAAAAAAAAAAAAAAAAA | 111 | DNA |
| 8 | /5Biosg/TCCCTACACGACGCTCTTCCGATC TTTTTTTTTTTTTTTTTTTV | 44 | DNA |
| 9 | AGATCGGAAGAGCACACGTCTGA/3InvdT/ | 24 | DNA |
| 10 | TTCAGACGTGTGCTCTTCCGATCTNNNNNNNNNNNN | 36 | DNA |
| 11 | AATGATACGGCGACCACCGAGATCTACACT CTTTCCCTACACGACGCTCTTCCGATCT | 58 | DNA |
| 12 | CAAGCAGAAGACGGCATACGAGATGTGACT GGAGTTCAGACGTGTGCTCTTCCGATCT | 58 | DNA |

Figure 10

COPY NUMBER PRESERVING RNA ANALYSIS METHOD

RELATED APPLICATIONS

This application is a national stage filing under 35 U.S.C. § 371 of international PCT application PCT/EP2015/055961, filed Mar. 20, 2015, which claims priority to EP Application No. 14161135.0, filed Mar. 21, 2014. The content of each of the prior applications is incorporated by reference herein in its entirety.

FIELD OF INVENTION

The present invention relates to a method of RNA analytics, in particular transcript amount and type estimation assays.

BACKGROUND

Gene expression is the process by which information from a gene is used in the synthesis of a functional gene product. These products are functional RNA of which one major important class consists of the protein coding messenger RNAs, mRNA, which are in the process translated to all kinds of proteins like enzymes, transporting molecules, and others. The knowledge of the mRNA content and its processing stage in cells and tissues is important for the understanding of cell genesis, the development of diseases, the drug response of organisms and other biological processes.

Biological cellular processes are affected by numerous internal and external parameters. Herein the entire RNA and in particular the mRNA pool (transcriptome) plays a central role. Typical mammalian cells contain between 10 and 30 pg total RNA which corresponds to $3.6 \cdot 10^5$ mRNA molecules on average. Current human genome data bases contain 20769 coding genes annotations, 48'461 Genescan gene predictions. While the numbers for gene annotations and gene predictions are quite stable the number of transcripts (now 195565 transcripts) that are annotated continuously increase due to improvements in RNA analytics [Ensembl release 73, September 2013]. The main focus of many investigations is the quantification of protein coding RNA, the mRNA or transcripts. Individual genes can express numerous different transcripts, so called splice variants, which are characterized through differences in their exon region, and/or differences of the start- and end sites of the untranslated regions which are important for regulatory processes.

Different methods have been developed to measure either mRNA or gene expression levels with different degrees of accuracy.

Expressed sequence tags, EST, are short sub-sequences of cDNA and result from one-shot sequencing of a cloned cDNA. They were used in the past to identify gene transcripts. Millions of ESTs are available in public databases and provide information on the conditions in which the corresponding genes are expressed. The ESTs enable the design of probes for DNA microarrays to measure gene expression.

Classical methods for gene expression measurements such as microarray hybridization assays, or more recent methods such as mRNA sequencing by massive parallel sequencing or next-generation sequencing, NGS, are limited through the inherent inaccuracy of the methods which can currently only to some extent be compensated through more measurements, like deeper sequencing, which inevitably increases the costs to such extent that analyses cannot be carried out on large sample throughput scales. However, accuracy in the measurements and also costs are the upmost requirements in pharmacological research and large, clinical scale studies. Microarrays can only detect genes on the exon or sequence level for which predetermined sequence probes have been designed before the experiments. The limited number of such hybridization probes and mis-hybridization often led to ambiguous results for high resolution gene expression experiments. Microarrays are limited by design because they can cover only a certain number of different 3'UTRs (3' untranslated region) and cannot identify new 3'UTRs.

At the end of 1996 new high-throughput sequencing technologies [WO 98/44151] started to emerge and became known as next-generation sequencing, NGS, in contrast to the thitherto common dideoxy method after Sanger. The development of new sequencing technologies made it possible to attempt the sequencing of entire transcriptomes. NGS uses miniaturized and parallelized flow cells for sequencing millions of short, between 50 and 400 bases long, single or paired end reads. Spatially separated, clonally amplified DNA templates are sequenced by synthesis in such way that decoding occurs while adding individual nucleotides to the complementary strands. Optical scanning (Illumina systems from Illumina, Inc., US; SOLiD systems from Life Technologies, US; Roche 454 from 454 Life Sciences, Roche Diagnostics Corp., US) and the detection of tiny pH changes through arrayed microchip field effect transistors (Ion Torrent from Life Technologies, US) are used in different microfluidic platforms. The millions of short reads must be aligned to either known sequences or de novo assembled. For RNA research, however, the situation is more complex because sequences of transcripts from individual genes overlap to large extents. Annotations of previously found transcript variants provide frameworks to guide the subsequent transcript assembly on the basis of the discovery of individual exons, exon-exon junctions and coverage probabilities. Only the correct transcript assembly allows assigning reads to their parental RNA molecules and, further, the calculation of the respective copy numbers.

Independent of the NGS technology, the simultaneous determination of sequence and frequency information is one major problem in researching complex sequence mixtures. Because only its sequence determines the nature of the molecule it seems to be inevitable to repetitively sequence identical molecules proportional to their abundance for counting their corresponding copy numbers. A dynamic range of six orders requires a repetitive sequencing through millions of identical highly abundant molecules before reaching statistically sound values for low abundant molecules. Such approaches are resource and time consuming during sequencing and subsequent data analysis. The required read depth depends heavily on the complexity of the sample [Hopper, 2010; Wendl, 2009]. After all, one major challenge is the entanglement of aligning overlapping reads to multiple overlapping transcript annotations within individual genes. The efforts and costs in read depth and computation are enormous. Therefore, different approaches have been developed which eliminate the need for aligning overlapping reads by just producing one read per mRNA molecule. Grouping and counting such reads simplifies the mRNA and gene expression measurements [WO02/059357].

Polyadenylation of pre-mRNA is one important step of eukaryotic gene expression and regulation. Many genes produce mRNAs with alternative polyadenylation sites, APA, and distinct 3'UTRs which can be differently regulated or which can encode also for different protein isoforms. Therefore, to combine the simplicity of determining gene expression values by generating just one read per mRNA with the precise identification of polyadenylation sites methods for exclusively targeting those APAs were developed.

One such method identifies polyA-sites in a genome-wide and strand specific manner [Wilkening, 2013]. Here, libraries for NGS sequencing are prepared through: heat fragmentation of the RNA sample, solid phase reverse immobilization, SPRI, purification to stop further fragmentation through buffer exchange, reverse transcription after priming with biotinylated and anchored polyT (V)-primer-adaptor, SPRI purification to remove of all non-polyA containing fragments and to exchange the solution, Rnase H treatment to degrade the RNA and to use the smaller RNA fragments as random start sequences for the second strand synthesis with DNA polymerase I which generates the longest possible double strand because all other inner extended priming sites will be displaced through strand displacement, SPRI purification, Streptavidin affinity purification and binding which enables the solution exchanges after each of the following 3 steps, enzymatic end repair, single dA tailing, ligation of another adaptor, followed by an enrichment PCR, and SPRI purification.

The resulting NGS libraries contain just one read per mRNA molecule, although one read per mRNA marks the theoretical maximum. In practical terms, because each of the many reaction steps of the library generation has an efficiency below 100%, the result is a distorted, and in the aspired realization proportionally distorted, representation of the transcript abundances. It is important that the number of reads per transcript species is proportional to their copy number and not to their length or any other sequence specific biases. The labor-, chemicals- and consumable intensive method is advantageous for gene expression measurements because it allows quantifying RNA abundances through simple read counting because only one read is produced from each transcript. The method continues with a particular NGS protocol which silently reads through the polyT-stretch of the primer-adaptor before the real sequencing starts. This part is termed 3'T-fill method. In addition, expression levels of polyA-site isoforms can be detected and quantified with a resolution of single nucleotide sequence, or after merging polyA-sites of close proximity to respective clusters. Beside better quality in the read generation the main improvement in the protocol was the introduction of said 3'T-fill which enabled the sequencing from the very end of the transcripts.

Other polyA-site enrichment methods had been developed before but without the aforementioned 3'T-fill. Because internal references of transcript variants are missing it is hard to judge the different qualities of the methods. One simpler method is the multiplexed analysis of polyA-linked sequences, MAPS [Fox-Walsh, 2011]. Herein, a biotinylated oligo-dT (NV) containing adaptor sequence is used to prime cDNA synthesis. Upon solid phase selection, second strand synthesis is initiated by using a random primer which is linked to another adaptor sequence. Finally, the library is released from Streptavidin-coated beads and amplified using a bar-coded primer together with a common primer. This method has likewise the ability to robustly detect gene expression. Although, the read direction was originally directed towards the 3'-end of the mRNA, and only a very narrow size selection of the library would enable to read into the polyA-site, the exchange of the adaptor (primer) sequences and the combination with above described 3'T-fill method allows also the precise detection of the polyA sites with all reads.

The method has several pitfalls. It aims to synthesize full length cDNA, is protecting the ends of the cDNA with didesoxyribonucleosidetriphosphate, ddNTP, before binding the cDNA to Streptavidin-bead surfaces, purifying the cDNA by these means, priming and extending second strands with Taq DNA polymerase. Taq DNA polymerase degrades any encountered downstream strands via a 5'->3' exonuclease activity and has been chosen to ensure that only one second strand per cDNA, the one which has been primed farthest from the polyA-site, is produced before purifying the double stranded product through the mentioned affinity binding method. Because of the long cDNA the NGS libraries are by trend long which would lead to length biases in the later NGS cluster generation. While the second strand synthesis occurs on the bead surfaces it is hindered in particular in the region of the interface towards the sequence of the first, biotinylated, primer sequence. The multiple purification steps which are assisted by surface confined reactions introduce a series of length and sequence biases in the generation of authentic polyA-site reads.

Another deep sequencing based method is the quantitative polyA site sequencing, PAS-sequencing [Shepard, 2011]. This method starts with a fragmentation step to generate RNA fragments of the desired size range. Again, the first adapter sequence is part of anchored oligo-dT (NV) primer. This method takes advantage of the terminal transferase activity of reverse transcriptases. Upon reaching the 5'-end of the mRNA fragment the MMLV-V reverse transcriptase adds a few untemplated deoxycytodines to the 3'-ends of the cDNA. Those ends hybridize with second adapter which contains a triple G sequence. The reverse transcriptase continues by switching the template and synthesizing a copy of the mRNA fragment which is now extended by both adapter sequences.

A major drawback of this very simple method is its inefficiency of only 1-10%, bias and inaccuracy of the template switch. Low efficiency will result in losses of low abundant transcripts. Template switching is not exclusively coupled to the template switch primer and artificial fusion transcripts may be generated by switching to different RNA templates. Also, the template switch primer has to be provided in a large excess, making a purification step before the subsequent library amplification essential.

Another polyA-seq method has been described by Derti et al. [2012]. The protocol employs first strand synthesis with anchored polyT-primers containing the first adaptor sequence, RNAse H treatment to digest RNA before, priming with a random primer which contains the second adaptor sequence, and Klenow-extension for the second strand synthesis. Although the Klenow DNA polymerase I fragment lacks 5'->3' exonuclease activity it contains persistent strand displacement activity. Therefore, each first strand cDNA can generate several randomly primed second strands. The unambiguous bijective mRNA abundance and read counting correlation is not ensured.

U.S. Pat. No. 6,406,891 B1 relates to a method for generating a full-length cDNA with a method comprising cycling back and forth between a processive RT and a thermostable RT enzyme during first strand synthesis.

EP 1371726 A1 relates to a first and second strand synthesis method. For first strand synthesis bead immobilized primers and for second strand synthesis random hexamers are used. Second strand synthesis is with a mixture of Klenow, which contains strand displacement activity.

Costa et al. [2010] relates to transcriptome studies using RNA-seq.

Mainul Hoque et al. [2012] relates to the analysis of alternative cleavage and polyadenylation by 3' region extraction and deep sequencing.

For gene expression counting the need for reliable, efficient, simple and cost effective methods to produce NGS library amplicons which possess a bijective correlation between mRNA abundance and read count exists.

SUMMARY OF THE INVENTION

The present invention provides a method of generating a nucleic acid product of a template RNA molecule, comprising—after having optionally obtained a template RNA—
a) annealing a first oligonucleotide primer at a preselected nucleic acid region of the template RNA,
b) elongating the first oligonucleotide primer in a template specific manner thereby obtaining a first elongated strand, which is then usually in a double strand comprising the template RNA,
c) removing the RNA template at least from the double strand,
d) annealing one or more further oligonucleotide primers to the first elongated strand,
e) elongating the one or more further oligonucleotide primers in a template specific manner 1) without displacement of primers annealed to the first elongated strand or 2) with a polymerase that destroys a displaced strand, thereby generating further elongation products,
f) isolating and/or amplifying an elongation product of said further elongation product comprising a nucleic acid portion that is elongated complementary (or in complementarity) to the first oligonucleotide primer.

The invention also relates to a kit comprising a reverse transcriptase, dNTPs, cofactors such as salts of metal ions required by a polymerase, preferably $Mg^{2+}$, a primer, preferably a poly-T primer, a DNA polymerase without strand displacement activity such as T7, Q5 or T4 DNA polymerase or a polymerase that destroys the displaced strand such as full length Bst, E. coli I DNA polymerase, and random oligonucleotide primers. The kit may be suitable for performing the inventive method according to any embodiments with any one or combination of preferred features.

The following detailed disclosure reads on all aspects and embodiments of the present invention. Methods descriptions also read on the kit, which may comprise parts suitable for performing said method; kit components may also read on the method, which may implement or use such components according to their function.

DETAILED DISCLOSURE OF THE INVENTION

The invention relates to a simple and cost-effective method to provide (just) one amplification product per RNA molecule, which is achieved by the 3' end specificity of the priming reactions if e.g. an oligo-dT containing primer is used or gene/transcript specificity if a gene or transcript specific sequence is targeted during first strand synthesis and the subsequent isolation, selection or amplification of such products by aiming at the elongation product comprising a nucleic acid portion that is elongated complementary (or in complementarity) to the first oligonucleotide primer (e.g. by selecting a sequence tag or linker sequence or selecting another sequence of the primer such as a sequence being complementary to the first primer). By preventing displacement of primers annealed to the first elongated strand—or by destroying displaced strands, only one product, i.e. extending from the primer of step d) which binds closest to the preselected region of the template is obtained which meets the selecting, isolating, amplification or generally processing criterion of step f). Thus the concentration or copy number of each RNA template species (having the preselected sequence) correlates directly with the elongation product finally obtained by the inventive method. The method is described above in the summary and further in the claims. The method can be performed in one single gradually increasing volume or container, in particular by just adding further reagents to the reaction mixture, without the necessity of purification by isolation of components from the mixture in steps a) to e). The further reagents may to some extent neutralize or build on the components which are already in the fluid. This approach not only simplifies the processing but increases the reliability of the method as all intermediate reaction products always are kept in one coherent volume phase. Besides mitigating in manual preparations any purification(s) in between, this greatly facilitates implementation of the method onto a chip or microfluidic device suitable for automation.

Gene expression is measured by aligning and grouping amplification products or reads to gene annotations and counting of those reads without the need of aligning reads to transcript scaffolds, and without applying subsequent transcript specific normalization algorithms which try to eliminate certain length and sequence specific biases, which are necessary for methods with more than one read per RNA molecule.

The inventive method is short as it requires two priming events, two polymerase reactions, one intermediate RNA hydrolysis, which is followed by one final isolation, amplification or purification, aiming at selecting the products corresponding to the preselected nucleic acid region of the RNA template.

It is known that only one read per transcript provides higher accuracy in gene expression counting. One new aspect of the inventive method is the reduction in the required read depth because of the occurring length normalization as only a portion is analyzed, having a limited length as compared to full-length cDNAs.

Restricting the gene expression signal to the preselected nucleic acid region of the mRNA enables lower relative sequencing costs, currently estimated to be around $⅕^{th}$ compared to conventional full length sequencing, and a more correct gene expression value because the length normalization occurs at the level of the sample preparation. Therefore, no precognition is necessary on the length of transcript variants for calculating correct FPKM values (Fragments Per Kilobase of transcript per Million mapped reads). The information content provided by the region of mRNA is enough for the purpose of classifying samples in large scale analysis as, although the information content is less than a full scale transcript analysis but more than simple gene expression would provide.

The generated nucleic acid product may also be seen as an amplification product since nucleic acid amplification reactions are used, but of course the template RNA itself is not copied in its entirety and hence not multiplied by the process. The method aims at "amplifying" or simply generating a polynucleotide comprising a copied sequence of a region of the template RNA. This copied sequence is a portion of the template RNA and lies in the 5' direction of the preselected nucleic acid region that is used in primer binding step a). The copied sequence usually has a length of about 25 to 2000 nucleotides, approximately about 100, 200, 300, 500, or 1000 nt. Exact values may differ and are influenced by parameters and the reagents used by the practitioner. In essence a practitioner can tailor the region length obtained by e.g. modifying the amount and constitution of the primer used in the reaction, especially the primers of step d), that may be random primers. The practitioner can tailor the average region length to be optimal for subsequent NGS or any other sequencing.

When, according to one possibility of the invention, each transcript (template RNA molecule) or targeted sequence (preselected nucleic acid region—may also be two or more per transcript) generates just one read (based on the elongation product) compared to multiple reads along the entire transcript and these reads may start or end all with the same nucleotide, there might arise ambiguity if these reads originate from different copies of a transcript or if they originate from PCR duplication events. Therefore optionally barcodes can be used during the first extension reaction to tag (barcode) each priming event in order to distinguish multiple transcript copies from clonal PCR duplication events to determine the true extent of re-sampling [US 2011/0160078, incorporated herein by reference]. Ideally such barcodes are introduced as random barcodes in the linker sequence. Preferably they do not participate in the priming reaction. Each read (or elongation product) will than have an individually unique barcode distinct from other reads (elongation products).

Proportional PCR duplication is not inflicting the claimed higher accuracy but indicates that the applied read depth exceeds the complexity of the NGS library, so the sequencing run starts to sequence (read) copies of the same inserts again.

PCR duplication per se is not a problem, but seeing reads which start and end with the same sequence may make the user belief that he sequences too deep, or that the library complexity is too low. Because all reads from a transcript start with the same sequence adjacent to the polyA tail (or other targeted sequences), and often end at preferred sequences the reads appear more often as being PCR duplicates although they are not. Signatures such as random barcodes that are introduced during first strand synthesis therefore enable to distinguish genuine singular reads from duplicates.

The preliminary step, obtaining or providing a template RNA, is the provision of a sample containing any RNA, such as total RNA from a cell. Also, special RNA fractions, such as the mRNA fraction or one of the following RNA types may be selected. Although, the RNA is preferably a transcript or mRNA, especially preferred such that it comprises a polyA-site or -tail, of course other RNA molecules can be used and analyzed, such as pre-miRNA, miRNA, pre-tRNA, tRNA, pre-rRNA or rRNA, any one of which, alone or in combination with other RNA types, may be comprised in the RNA. Preferably the template RNA comprises a polyA-site or -tail. If not present per se in the RNA species, a tail may be added artificially by a tailing reaction. Of course also other tails than polyA may be added, e.g. by a ligation reaction using a ligase (optional component of the kit) as e.g. described in WO 2007/062445. The first primer of step a) should then anneal to a sequence of this (artificial) tail. In the next steps, preferably a cDNA is generated during the inventive method by using a DNA polymerase, preferably a RNA-dependent DNA polymerase. Alternatively specific regions of transcripts of interest, e.g. transcripts involved in the generation of diseases such as cancer, immune-deficiencies, can be targeted during the initial priming of the RNA using transcript specific primers.

The RNA template may be of any length, but preferably is in the range of 20 to 100000 nt (nucleotides), especially preferred 30 to 50000 nt, more preferred 50 to 25000 nt, 75 to 10000 nt or 100 to 8000 nt.

Preferably the (optional) tailing of the 3' end is performed using terminal transferase (optional component of the kit). Although other tailing methods are also disclosed, like ligation of a tail sequence, which can be e.g. a defined preselected sequence. The terminal transferase can add a certain number of nucleotides preferably uniformly selected from one nucleotide type. Any other means for tailing, adding a tail sequence can also be used, e.g. by ligating the tail sequence which can be uniformly of one type of nucleotides or of varying nucleotides. Such a tail is preferably a sequence in the range between 5 and 500 nucleotides, more preferred less than 400, less than 300, less than 200, less than 100, less than 50 or less than 30 nucleotides. Any such tail (or part thereof) can be used as the preselected 3' terminal nucleic acid region in step a) to which a primer can be annealed.

The inventive method is particular suitable to analyse complex mixtures of various RNA molecules with different nucleic acid sequences. Preferably, 1, 2, 3, 4, 5, 6, 7, 8, 9, 10 or more, especially at least 20, at least 30, at least 40, at least 50, at least 75, at least 100, at least 200 or more different RNA templates of different sequences are obtained and/or used in the inventive method.

Step a), annealing a first oligonucleotide primer at a preselected nucleic acid region of the template RNA, contains providing a first primer that anneals or hybridizes under hybridization conditions (below melting temperature of the double strand) to the preselected region. It thus comprises a complementary sequence in sufficient length for the annealing reaction or hybridization. The complementary region may be any one commonly used in the art, such as 6 to 40 nt in length, preferably at least 6, 7, 8, 9, 10 or more nt. The preselected region is one of a known or expected sequence, such as a polyA-tail common to eukaryotic mRNA. Any other known sequence may be used, such as gene or transcript specific sequence or sequences that select for one or more specific targets of interest. Such one or more target sequences can be used to create disease specific panels, such as for e.g. cancer or immune-deficiencies. The preselected nucleic acid region can be present on one or multiple template RNAs of interested. These templates of interest might share a common property, such as being related to a specific disease or condition. Preferably the this panel of templates of interest comprises 2, 3, 4, 5, 6, 7, 8, 9, 10, or more such as at least 15, at least 20 and any range in between, templates comprising a preselected nucleic acid region. Multiple first primers might be used to anneal to this panel in one reaction (multiplexing).

Preferably, but not necessarily, it is a preselected 3' terminal region of the template RNA, such as a polyA-tail or another added tail during tailing as described above. The preselected region may have a sequence that is characteristic for a RNA type of interest (e.g. as disclosed above). Also, as said above, the preselected region may be attached artificially to the RNA template e.g. by ligation or tailing.

The primer may contain one region with a sequence that anneals to the RNA template, e.g. a complementary sequence that hybridizes by base pairing, and optionally a region that does not bind, e.g. by having a non-complementary sequence and/or a sequence that is blocked by an oligonucleotide in hybrid with this region that prevents further hybridization. This non binding region preferably includes a (preferably random) barcode to distinguish multiple transcript copies from PCR duplication events. Preferably such barcode is located in the blocked region. The annealing region may e.g. be an oligo-dT$_8$ to oligo-dT$_{35}$ region, preferably oligo-dT$_{15}$ to oligo-dT$_{30}$ region, e.g. oligo-dT$_{10}$ or oligo-dT$_{25}$, which increases selectivity and decreases internal priming events, which can occur at internal A-rich sites within the mRNAs, if they are not desired preselected regions of the template RNA.

Preferably the first primer is a DNA primer, optionally modified as described below for random primers.

Step b), elongating the first oligonucleotide primer in a template specific manner thereby obtaining a first elongated strand, can be done with any template specific oligonucleotide elongation reaction, preferably using a nucleotide polymerase, preferably a DNA polymerase, especially a reverse transcriptase with the RNA as template for reverse transcription. The first elongated strand is then usually in a double strand comprising the template RNA as complementary strand. The first elongated strand is a template for a further primer elongation reaction in following steps. The reverse transcription can be performed using any reverse transcriptase, as described further below—with or without strand displacement activity—e.g. with M-MLV RT. Preferably at least some strand displacement is present to allow the polymerase to uncoil RNA secondary structures. In case of reverse transcriptases using RNA template, in preferred embodiments the reverse transcription is carried out under conditions that do not allow for secondary or tertiary structure formation of the RNA template (RNA:RNA hybrids) or under conditions that allow for these secondary structures to be strand displaced by the reverse transcriptase. The polymerase used during the elongation reaction may be a viral polymerase, and may be selected from the group consisting of AMV RT (and mutants thereof such as Thermoscript RT), M-MLV RT (and mutants thereof including but not limited to Superscript I, II or III, Maxima RT, RevertAid, RevertAid Premium, Omniscript, GoScript), HIV RT, RSV RT, EIAV RT, RAV2 RT, Tth DNA polymerase, C. hydrogenoformans DNA polymerase, Avian Sarcoma Leukosis Virus (ASLV) and RNase H-mutants thereof. Mixtures of any of these polymerases may be used. In particular, mixtures of viral polymerases may be used, such as mixtures of M-MLV and ASLV, and/or their RNase H reduced or RNase H minus analogs may be used. In any of these methods and compositions, two or more polymerases may be used, including any polymerase as described above.

Step c), removing the RNA template at least from the double strand, means that the first elongated strand, at least in a 3' terminal region, is freed from the RNA template. The double strand can be melted and the RNA template removed by purification, but such purification is less preferred as it adds further laborious steps, or digested. Digestion can proceed completely or partially. Short RNA portions may remain on the first elongated strand as the inventive method does not require full-length access to the first elongated strand. Digestion can be performed using an RNase or heating, especially in the presence of further RNA destabilizing agents, such as alkaline conditions or divalent cations, such as Mn$^{2+}$. Preferably, removing the RNA template comprises enzymatic RNA digestion, preferably by an RNase, alkaline degradation, preferably by NaOH treatment, or heating in the presence of divalent cations, preferably Mn$^{2+}$ or Mg$^{2+}$.

The reaction in step e) ensures that only one elongation product is produced by using conditions without strand displacement or by destroying, i.e. depolymerizing, the displaced strand, e.g. by using a suitable polymerase, in which case strand displacement may occur. Without strand displacement only the most 3'-directed primer to the preselected region is successfully extended to the location corresponding to the first primer. In order to prevent the RNA template to interfere with this reaction, preferably after the reverse transcription the RNA is removed, preferably hydrolyzed, completely or at least to such extent that only short fragments remain which possess lower melting temperatures than the next following second primers during second strand synthesis.

RNA undergoes spontaneous degradation at high temperatures if divalent cations are present. The divalent cations can later be masked if not removed by chelating agents, such as EDTA or EGTA. If the samples are not purified further with precipitation or column-based purification methods, the final concentration of the chelating agent should be balanced in such way that it provides protection from degrading any later products and not inhibiting subsequent enzymatic reaction which may also require divalent cations for their activities (e.g. Mg$^2$ for polymerases). Rapid hydrolysis of RNA occurs e.g. in the presence of divalent cations at temperatures of at least 70° C., e.g. at 75° C. and/or up to 98° C.

Hydrolysis of the RNA is preferably performed using MnCl$_2$ and high temperatures, which leaves the cDNA intact while destroying the RNA. This is a much more cost effective approach than using RNases. Alkaline conditions, such as by NaOH addition, can also be used to hydrolyze RNA, but much greater care must be taken to protect the cDNA from degradation as well, e.g. using lower temperatures or less alkaline pH, being adjusted so that the RNA degrades but not the cDNA.

Step d), annealing one or more oligonucleotide primers to the first elongated strand, requires the binding of at least one primer to the first elongated strand. This step essentially is performed according to the same principles as described for the first primer annealing in step a). The sequence of the further primer(s) can be one that is known for the RNA template of interest or it may be unknown. It is preferred to use random primers, which do not require knowledge of the complementary sequence. As with step a) described above, multiplexing is possible. Also in step d) multiple further oligonucleotide primers, that optionally specifically anneal to one or more specific target regions of choice, thereby allowing specific selection of one template RNA or gene sequence thereon per further oligonucleotide primer, is one option.

In random priming an oligonucleotide population of random sequence, usually a random pentamer, hexamer, 7-mer, 8-mer, 9-mer, 10-mer, 11-mer, 12-mer or longer oligomer sequence, is used to prime the elongation reaction anywhere within the template nucleic acid strand, here the first elongated strand. The primer may of course comprise further nucleotides in addition to this random oligomer sequence. Optionally, additional random barcodes can be used to distinguish multiple transcript copies from PCR duplication events. Preferably the further primers are DNA, optionally modified as described below.

"Random primers" is to be understood as a mixture of different primers with different primer sequence portions, with a high variance due to a random synthesis of at least a portion of the primer sequence. Random primers potentially cover the entire combinatory area for said sequence. The random sequence primer portion of the random primer may cover 1, 2, 3, 4, 5, 6, 7, 8 or more random nucleotides or universal nucleotides. Random nucleotides are randomly selected from A, G, C or T (U) at a given nucleotide position.

In terms of hybridizing sequences of primer sequences T and U are used interchangeably herein. The combinatory possibilities for a random sequence portion is $m^n$, wherein m is the number of nucleotide types used (preferably all four of A, G, C, T(U) and n is the number of the random nucleotides. Therefore a random hexamer, wherein each possible sequence is represented, consists of $4^6=4'096$ different sequences. A random primer may also comprise one or more nucleotides, which do not specifically bind to a complementary nucleotide as A, T, C or G do. Such nucleotides are also referred to as "wobble bases" or "universal bases". Nucleotides with universal bases can be used, such as deoxyinosine, 3-nitropyrrole 2'-deoxynucloside and 5-nitroindole 2'-deoxynucleoside. Universal bases will basepair with any nucleotide of A, C, G, T(U) or at least two or three nucleotides thereof. It is not necessary to include all possibilities for such a random primer. In some embodiments the random primer comprises at least one random nucleotide (permutation at one position as described above) and/or at least one wobble nucleotide. In the context of random primers or primers of a selected sequence, at least 10, preferably at least 20, especially preferred at least 100, different primers are used.

Especially for but not limited to optimal representation in a randomly primed elongation primers may be present in a concentration from 10 nM to 100 μM, and more preferred at about 1 μM but can also be at least 200 nM. In preferred embodiments the ratio (w/w) of primer to template nucleic acids is between 5:1 and 1:1'000, preferably between 2:1 and 1:500, preferably between 1:1 and 1:300, preferably between 1:2 and 1:250, preferably between 1:5 and 1:150, preferably between 1:10 and 1:100, preferably between 1:12 and 1:50. The molar ratio of primer to template nucleic acids may be between 100:1 to 1000000:1, preferably between 1000:1 to 1000000:1, between 10000:1 to 500000:1, or between 20000:1 to 300000:1. In one example, using 100 ng of mRNA starting material and assuming an mRNA length of 500 to 5000 nt with mean value of 2000 nt and adding 1 nmol of primers then are primers present in a molar excess of 6800:1.

The further primers may contain one region with a sequence that anneals to the first elongated strand, and optionally a region that does not bind, e.g. by having a non-complementary sequence and/or a sequence that is blocked by an oligonucleotide in hybrid with this region that prevents further hybridization. This non binding region can also include barcodes, preferably random barcodes to distinguish multiple transcript copies from PCR duplication events.

Step e), elongating the one or more further oligonucleotide primers in a template specific manner without displacement of primers annealed to the first elongated strand or with a polymerase that destroys a displaced strand, thereby generating further elongation products, follows similar concepts as step b). Any elongation method suitable for the given template, e.g. DNA, can be used. In preferred embodiments a (DNA-dependent if template is DNA or RNA-dependent if template is RNA) polymerase is used, preferably a DNA polymerase if the further elongation product shall be DNA.

The prevention of primer displacement in this step can be achieved by various provisions, e.g. the selection of a polymerase without displacement activity or by providing primers with a resistance to displacement by a polymerase or by using a polymerase that destroys the displaced strand.

As DNA polymerases can displace a DNA oligonucleotide from a template strand of DNA at least as good as dissolving secondary or tertiary structure, the hybridization of the oligonucleotide can be enhanced in order to stop strand displacement of the polymerase. A DNA polymerase with particular strong strand displacement activity is the Klenow polymerase (Klenow fragment). Prevention of displacement can be achieved by using modifications to the oligonucleotide itself or by using additives that either stabilize the hybridization of the oligonucleotide or that stop the polymerase. Modifications to the oligonucleotides that reduce or inhibit the strand displacement activity of the polymerase are for instance 2' fluoro nucleosides, PNAs, ZNAs, G-Clamps (U.S. Pat. No. 6,335,439, a cytosine analogue capable of Clamp Binding to Guanine) or LNAs (US 2003/0092905; U.S. Pat. No. 7,084,125). These modifications in general increase the melting temperature of the oligonucleotide, by increasing the local hybridization energy of the oligonucleotide to the template RNA or DNA strand as compared to the same oligonucleotide without the modification or stiffen the sugar phosphate backbone of oligonucleotide. Some also stiffen the sugar phosphate backbone further inhibiting strand displacement by the polymerase. Means for strand displacement stop (SDS) are disclosed in WO 2013/038010 A1 (incorporated herein by reference).

Alternatively or in addition, the hybridization of the primer to the template (e.g. first elongation product) can be altered by using different additives that bind or intercalate to the nucleic acids. For instance, ethidiumbromide, SybrGreen (U.S. Pat. Nos. 5,436,134; 5,658,751; 6,569,627) or acricidine, preferably intercalators that are specific for RNA:DNA or DNA:DNA hybrids, can be used. Other compounds that can bind to dsNA are actinomycin D and analogues, aminoglycosides of the Neomycin family (Neomycin, Ribostamycin, Paromomycin and Framycetin. Additives that alter the hybridization properties of the primer can also be covalently included into the primer structure.

The hybridization energy and kinetics can be changed to inhibit the strand displacement by the polymerase by the addition of nucleic acid binding proteins such as single stranded binding protein such as TtH SSB or Tth RecA.

It will be apparent to those skilled in the art that those additives are just examples and any other compound, base modification or enzyme leading to an increased stability of the primer-template hybrid can be used to increase the Tm and hence inhibit strand displacement or inhibit the strand displacement capability of the involved enzyme.

The increase in the Tm should be strong enough to prevent a displacement of any one of the 5' end nucleotides of the primer region annealed to the template by an elongating polymerase. In particular, the inventive Tm increase prevents displacement of the $3^{rd}$, $2^{nd}$ and/or $1^{st}$ nucleotide downstream to the 5' end of the primer region that is annealed to the template (further non-annealed 5' nucleotides may exist—e.g. linker regions or barcodes—that need not be modified).

In certain embodiments of the invention the strand displacement needs to be stopped right at the first 5' nucleotide of the downstream primer.

Therefore it is preferred that the binding of the oligonucleotide primers are specifically Tm enhanced at their 5' ends of the region annealed to the template to prevent the elongating polymerase from displacing them. Such modifications include but are not limited to LNAs, PNAs, ZNAs, acridine or fluorophores.

Oligonucleotides with an increased Tm at their 5' end such as LNA-modified oligonucleotides enable a stop right at the start of the next primer. It is within the scope of the invention to combine the strand displacement stop by using the LNA-modified oligos together with a polymerase without strand displacement activity as well as lowering the reaction temperature and using different additives to increase the binding of primers to the template.

Preferably C and/or G nucleotides are modified. Even unmodified these nucleotides have a higher Tm than A or T due to increased hydrogen bridge formation when complementary annealed. In preferred embodiments the oligonucleotide primer comprises at least one, at least 2, at least 3, at least 4, at least 5, at least 6 modified nucleotides being selected from G or C. These modified nucleotides are preferably at the 5' end of the primer sequence that anneals to the template as mentioned above.

Most efficient strand displacement stop is achieved by G or C bases as they increase the local Tm of the primer or stopper. Hence semi-random primers (hexamers, heptamers, octamers, nonamers, etc.) containing at least two, more preferably three or more Gs or Cs or a combination of Gs and Cs. It is most preferred if these Gs or Cs are modified to increase the local melting temperature, as is the case when using LNA modified bases. It is most preferred that at least 1, at least 2 or at least 3 LNA modified bases are used at the 5' end of the primer region that is annealed. Therefore, it is preferred that at least two, at least 3 modified nucleotides are used optionally chosen from G or C.

Several methods and means exist to ensure that the elongation reaction is stopped when the elongation reaction reaches the position of an additional primer annealed to the template. This stopping is also referred to as a prevention of strand displacement herein. The inventive step of preventing the polymerase to strand displace the next primer(s) of an already copied polynucleotide portion ensures that any portion of a polynucleotide molecule that already got copied is not copied again, and in particular that the most 5'-facing portion at the first elongated strand, which corresponds to the most 3' portion of the original RNA template, is not copied again. Therefore, no copied portion of the polynucleotide gets overrepresented in the second strand synthesis, and in particular said most 5'-facing copied portion is synthesized only once from each synthesized first strand template. This inhibition of strand displacement can be achieved through different means, such as decreasing the reaction temperature, using a polymerase without strand displacement activity, increasing the melting temperature or the hybridization energy of the primer:template hybrid or increasing the rigidity of the RNA or primer or stabilizing the helix. In practice, usually a combination of these means is selected to achieve optimal reaction conditions without strand displacement. A person skilled in the art is well enabled to select suitable parameters as described herein or known in the art to suit a particular template and reaction condition.

One option is to modify the reaction temperature. In general, a reaction temperature above 37° C., in particular above 70° C. is favored during elongation for better dissolving secondary structures in the template that leads to a more efficient displacement synthesis. In one embodiment stopping of strand displacement of the primer is achieved by decreasing the reaction temperature. Reaction temperatures below 37° C. and down to 25° C., and further to 4° C., are used to reduce strand displacement. However, even at lower reaction temperatures the strand displacement stop will not be complete when polymerases are used that have strand displacement activity and/or a simple stopper oligonucleotide is used that has no modifications that alter its melting temperature. It is preferred that the polymerization is carried out between 12° C. to 37° C.

In one embodiment instead of, or in addition to, decreasing the reaction temperature to achieve a better stop of the elongation at said position of a further primer or a stopper (and reduce strand displacement) polymerases that are deficient in strand displacement can be used. In case of DNA-DNA polymerases preferably T7, T4 or Q5 DNA polymerase is used in elongating the one or more oligonucleotide primers in a template specific manner. T4 DNA polymerase is especially effective and is preferred in all embodiments.

The polymerase may be a mesophilic or thermophilic polymerase, especially DNA polymerase.

Strand displacement deficient mutant polymerases may be able to displace the next primer for up to 3 nts when unmodified. It is within the scope of the invention to combine the strand displacement stop by decreasing the reaction temperature with the usage of displacement synthesis deficient mutants or any other polymerase with impaired displacement synthesis.

Increasing the concentration of monovalent counter-ions also will stabilize the any template-primer hybrids (but also the secondary structure. The concentration of monovalent positive ions is preferably selected from at least 20 mM, at least 30 mM, at least 40 mM, at least 50 mM, at least 60 mM, at least 70 mM.

Alternatively or in combination to any one of the above options, strand displacement prevention can be increased by the presence of a crowding agent, preferably PEG. Crowding agents are inert molecules that can be used in high concentrations and can be used to mimic the effects of macromolecular crowding inside a cell. Examples are PEG (polyethylene glycol), PVP (polyvinylpyrrolidone), trehalose, ficoll and dextran. Crowding agents are e.g. disclosed in U.S. Pat. Nos. 5,554,730 or 8,017,339. Other additives acting as crowding agent are Tween-20, NP-40 could be added additionally or instead of PEG. Within the scope of the invention preferably 12%-25% final PEG-8000 (v/v) are used. A variety of PEG molecular weights and compounds can be used, and the skilled experimenter will appreciate that the identity and concentration of the additive can be varied to optimize results. Crowding agents are preferably present in step e) as to decrease the risk of strand displacement. They can alternatively or in combination also be present in any other step, such as in a purification, especially in a precipitation step. The kit may comprise a crowding agent, preferably in a buffer for reaction step e), e.g. a buffer comprising a cofactor for a polymerase, such as $Mg^{2+}$. Later, the crowding agent may also be present in a precipitation buffer in which its concentration will be increased to such degree being sufficient for precipitation of polynucleotides, especially of the elongation products.

Step f), isolating and/or amplifying an elongation product of said further elongation product comprising a nucleic acid portion that is elongated complementary (or in complementarity) to the first oligonucleotide primer, is a selection of the correct elongation products of step e) that correspond to the preselected nucleic acid region of the original template RNA. Since strand displacement in step e) is discouraged or prevented, there will be essentially only one elongation product resulting from step e) for each template (directly, the first elongated strand but also implicitly the original template RNA) since other annealed primers will be prevented from elongating to the region corresponding to the preselected nucleic acid region due to the blocking action of the most 3' primer that can elongate to said preselected region to which the first primer bound, and can further elongate to along the entire sequence of said first primer. Other blocking events may be due to remnant fragments of the RNA template if the removal of step c) leaves some short degradation products annealed to the first elongated strand, which should be prevented from occurring through a complete RNA template removal since otherwise also the probability decreases for successfully elongating the last most 3' primer into the desired preselected region.

This "selection" of the correct further elongation product (per each template) can be achieved by e.g. an isolation, purification or an amplification or generally any processing specific for the further elongation product comprising a nucleic acid portion that is elongated complementary to the first oligonucleotide primer. An isolation may e.g. comprise a binding to an immobilized probe. An amplification can be used to obtain also a complementary strand of the further elongation product that is selectively produced recognizing the further elongation product as template strand using a primer. The amplification may be a PCR cycle which comprises a further primer annealing and strand elongation reaction. For isolation or amplifying, a known sequence may be used as recognition sequence, especially for oligonucleotide binding. Such a known sequence is e.g. a sequence that is identical to the original preselected nucleic acid region of the template RNA of step a), hence corresponds to the selective sequence region of the first primer, or corresponds to any other region that is included in the first primer—such as linker or barcode sequences that are further described below.

According to a preferment of any embodiment of the invention, the first oligonucleotide primer of step a) and/or further oligonucleotide primers of step d) contain a non-annealing sequence tag or linker sequence. Such sequence tags or linkers can be used for amplification primer binding in another elongation, especially PCR reaction. The sequence tag or linker may also comprise a unique sequence to each primer or primer type (especially in case of the random primers) or ubiquitous sequence identifier, also referred to as barcode or barcode sequence). The sequence identities or identifiers may identify primers (and subsequently elongation products) of a particular experiment or batch, or individual or groups of elongation products. The sequence tags allow further analysis by massive parallel sequencing. "Non-annealing" can be achieved by selecting a sequence that does not anneal to its hybridizing template (the RNA template, first or further elongating strand) and/or by hybridizing the non-annealing sequence to another oligonucleotide, thus blocking this part of the primer and preventing hybridization with the template.

It is also possible that the template RNA prior to first primer annealing (in step a) is a fragmented RNA, i.e. a RNA obtained e.g. from a sample is treated to undergo fragmentation to provide the template RNA. Such a fragmentation can be carried out using any means known in the art. Fragmenting can be initiated in a sequence dependent manner, e.g. by endonuclease digestion, or by sequence independent means such as by a physical means like sonication or shearing, or such as by chemical means like hydrolysis. If a sequence dependent method is used, e.g. restriction endonuclease digestion or sequence specific amplification, fragment ends will possess a sequence bias. One preferred embodiment is the fragmenting by limited degradation or hydrolysis as described above for step c), such as heating in the presence of divalent cations or under alkali condition, but for a limited time and/or lower temperatures to preserve larger RNA fragments. Such fragments may e.g. have an average length of about 100 to 5000 nt, preferably 300 to 3000 nt, especially preferred 500 to 2000 nt. The fragments need to maintain a minimum length of more than 50 nt, preferably more than 100 nt, especially preferably more than 150 nt to preserve the selective sequence portion to be intact in the targeted 3' end fragment, to provide a long enough sequence for random priming during step e), and to maintain a long enough sequence insert between the complementary first and the second primer sequence which can be mapped to a genome and/or transcriptome annotation. It is preferred that the sequence insert is more than 10 nt, more than 15 nt, preferably more than 20 nt long, which is often set as a minimum length requirement for bioinformatics NGS sequencing read aligning algorithms.

Preferably the method comprises performing a PCR on the further elongation product using a primer (or primer pair) specific for a sequence tag or linker sequences of said elongation product. Such linkers or sequence tags can be introduced by the primers—in step a) and/or primers in step d).

These additional primers of the further PCR may comprise additional sequence tags or linker sequences, which again can be used in PCR amplification. Also these tags or linkers may comprise a sequence identifier such as a barcode as described above for the first mentioned linkers or sequence tags.

In a preferment the inventive method further comprises in step f) purifying the elongation product of step e). Such purification can be a selection of polynucleotides with a length that corresponds to the expected length of the elongation product of step e), e.g. 150 to 500 nt. The length of the elongation product of step e) can be controlled by e.g. modifying the primer concentrations of random primers, i.e. more random primers will lead to more priming events on the first strand and hence the desired elongation product that is then selected in step f) will be closer to the first priming site and thus shorter in length. Purification can be done by precipitation of the elongation products while keeping short polynucleotides with a length of e.g. less than 100 nt in solution and removing the polynucleotides in solution. 50 to 100 nt is a typical length for primer-primer products including two sequence tags or linkers, one on each side. In a preferment, purification is for removing such short polynucleotides with a length of 70 nt or less or of 50 nt or less or of 40 nt or less or of 30 nt or less. The range between 40 and 70 nt is a typical length for primers and primers including a sequence tag or linker. Preferably the method comprises a solid phase reversible immobilization which selectively binds and releases polynucleotides of defined size ranges to and from solid surfaces such as surfaces with a moiety of hydroxyl groups [Hawkins, 1995]. Size dependent polynucleotide precipitation can be imposed through a crowding agent, preferably through PEG using specific buffer conditions which include defined salt concentrations and pH values. Preferably short polynucleotides to be removed are not bound, e.g. precipitated, onto coated beads and removed with the supernatant, before the desired longer oligonucleotides are released into a new buffer containing no, or less crowding agent. Preferably such beads contain a magnetic core [U.S. Pat. No. 5,705,628]. Other purification methods include size dependent chromatographic methods such as size exclusion chromatography.

One preferred embodiment of the invention—combinable with every other embodiment—is that the steps a) to e) of the method are performed in one subsequently increasing fluid volume for example in one well, one container, or one tube. All reaction steps starting after the provision of the RNA in a solution aliquot up to the isolation or amplification of the desired elongation product which comprises the nucleic acid portions that are elongated complementary to the first oligonucleotide primer are carried out in said one solution to which stepwise the other reaction components are added through adding further solutions. Adding the reagents necessary for performing the inventive method, e.g. starting substances, enzymes and cofactors in a fluid, creates a reaction mixture. Essentially, the method of steps a) to e) can be performed without additional purification steps. Hereby the actions taken for steps a) to e) themselves are not considered as purification—especially not the RNA removal of step c) since the degraded products of the RNA after degradation may remain in solution. In particular, the inventive method of steps a) to e) preformed in one increasing fluid volume or one container is preferably a method without fluid removal from the reaction mixture. Such method simplifies the handling of the procedure significantly. It also helps to maintain the sample and subsequent reaction products by not purifying the intermediate products and dividing the reaction volume.

The present invention further provides a kit comprising a reverse transcriptase, dNTPs, cofactors or salts of metal ions required by a polymerase, preferably $Mg^{2+}$, a primer, preferably a poly-T primer, a DNA polymerase without strand displacement activity such as T7, Q5 or T4 DNA polymerase, random oligonucleotide primers. The kit may be suitable for performing the inventive method according to any embodiments with any one or combination of preferred features. The primer, preferably poly-T primer or one or a mixture of multiple gene- or transcript specific primers, is suitable for step a) and the random primers are suitable to be used in step d). These primers or primer preparation differ in primer composition and are preferably provided in separate containers, such as vials.

The kit may further comprise a RNA degradation agent, such as an enzyme or a divalent cation, to be used for elevated temperature RNA degradation, and/or a crowding agent such as PEG. Of course any components described above may be used in alternative or more preferred embodiments.

One further advantage generating the nucleic acid product according to the invention accomplishes is a length normalization—all further elongation products obtain a similar length or a narrow length distribution—which frees sequencing space which would have been alternatively used by reads which are generated from the entire and longer transcripts. The gain as understood as saved sequencing space for obtaining the same information on gene expression and transcription end site distribution is a relationship between transcript length variation and dynamic or concentration range of the transcripts in one samples. The relationship is best illustrated when looking at two boundary conditions. i) If all transcripts would have the same known length, e.g. all transcripts are 1 kb long and all generated fragments/reads are uniquely mapping, then length normalization, to e.g. 100 bp, would have no benefit. Hence, the gain does not depend on the decrease of the average length but the decrease of the length distribution. ii) If all transcripts would have different and unknown lengths, e.g. transcripts are between 500 bp and 10000 kb long and many generated fragments/reads cannot uniquely assigned because they are mapping to exons which are shared by several transcript variants from the same gene, then length normalization, to e.g. 100 bp, would have the benefit to unambiguously count reads and determine the correct gene expression value in relation to the overall number of reads. Therefore, the concentration weighted length distribution, the correctness of the sequence annotation (preknowledge) and the ability of uniquely mapping reads which can be assigned unambiguously to the correct transcript are the relevant measures for the complexity of a transcriptome. This complexity can be significantly reduced by the invented method.

The commercial opportunity of the inventive method is seen in replacing gene expression profiling by micro arrays and providing an intermediate analysis tool below a full mRNA transcriptome analysis. Toxicogenomic and Pharmacogenomics are examples for possible applications. By using region, gene- or transcript specific primers in step a) and/or in step d) targeted sequencing panels are possible. Any combination with targeted (sequence specific, is preselected/predefined) and non-targeted (e.g. to ubiquitous sequence like a sequence shared by all RNA sequences of interest, like polyA, or random sequence) first and second primers is possible, such as a) target specific (=targeted) first primer and non-targeted second primer; b) non-targeted first primer and a targeted second primer; c) targeted first primer and targeted second primer; d) non-targeted first primer and non-targeted second primer. Of course, the benefit of performing the inventive method in one subsequently increasing fluid volume applies to all these variants, especially without fluid removal/washing. A use for b) is e.g. to detect potential variation on the 3' side, such as alternative splice events, alternative last exon alternative PAAs as well as fusion events. A use for a) is e.g. to detect potential variation on the 5' side, such as alternative splice events, alternative first exon as well as fusion events.

The present invention is further illustrated in the following figures and examples, without being limited to these embodiments of the invention.

FIGURES

FIG. 1: Outline of the inventive method. The reaction proceeds through subsequent addition of the reactants and is staged into a) cDNA synthesis is initiated by priming to a known region or tag which is either present already (here Poly(A) of mRNA) or attached in a preceding reaction. P1 is complementary to said known region and furthermore contains a non complementary specific sequence at its 5' end serving as a universal tag. b) RNA is reverse transcribed into cDNA by an RNA dependent polymerase i.e. a reverse transcriptase. c) After cDNA synthesis the RNA template is hydrolyzed or degraded either by RNAses, pH changes (NaOH and heat), or divalent cations ($Mn^{2+}$, $Mg^{2+}$ and heat). d) Then, the single stranded cDNA is primed by multiple random primers, P(n), P(n+1), ..., P(n+n), e) and a second strand is synthesized using a DNA dependent polymerase without strand displacement. f) The lack of strand displacement guarantees that only the most 3' fragment will contain both tags, one from the cDNA synthesis primer and the other one from the 2nd strand synthesis primer. This most 3' fragment is isolated and/or amplified.

Figure 2:
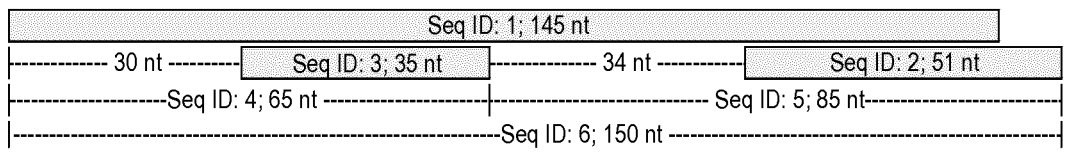

FIG. 2: Schematic representation of exemplary nucleic acid molecules occurring in the assay. Two oligos (Seq ID: 2 and Seq ID: 3) are hybridized to a single stranded DNA template (Seq ID: 9). A polymerase without strand displacement will generate a 65 nt long fragment (Seq ID: 4) resulting from the elongation of Seq ID:3 and a 85 nt long fragment (Seq ID: 5) from the elongation of Seq ID: 2. A polymerase with strand displacement will generate a 150 nt long fragment (Seq ID: 6) from the elongation of Seq ID: 2 and the displacement of Seq ID: 3. Additionally a 65 nt long fragment (Seq ID: 4) resulting from the elongation of Seq ID:3 and in case of inefficient strand displacement products between 85 nt (Seq ID: 5) and 150 nt (Seq ID: 6) could occur.

Figure 3:
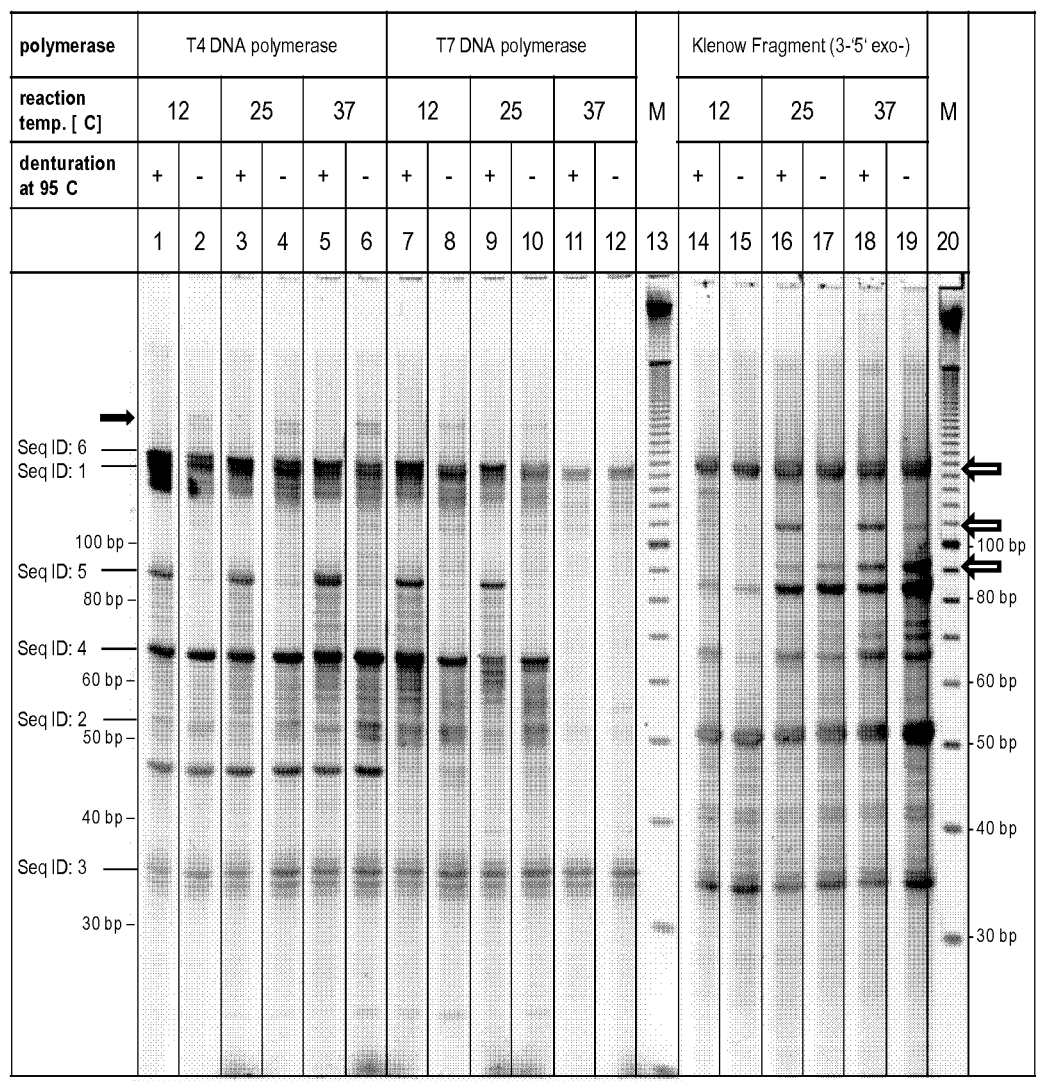

FIG. 3: Comparison of polymerases with and without strand displacement activity at different reaction temperatures. Three different polymerases, T7 and T4 DNA polymerase, both without strand displacement and Klenow fragment 3'-5' Exo- with strand displacement were tested at different reaction temperatures. White filled arrows indicate partially displaced strand displacement stop products. Secondary structures of the single stranded template without the denaturation step are indicated with a black arrow.

Figure 4:
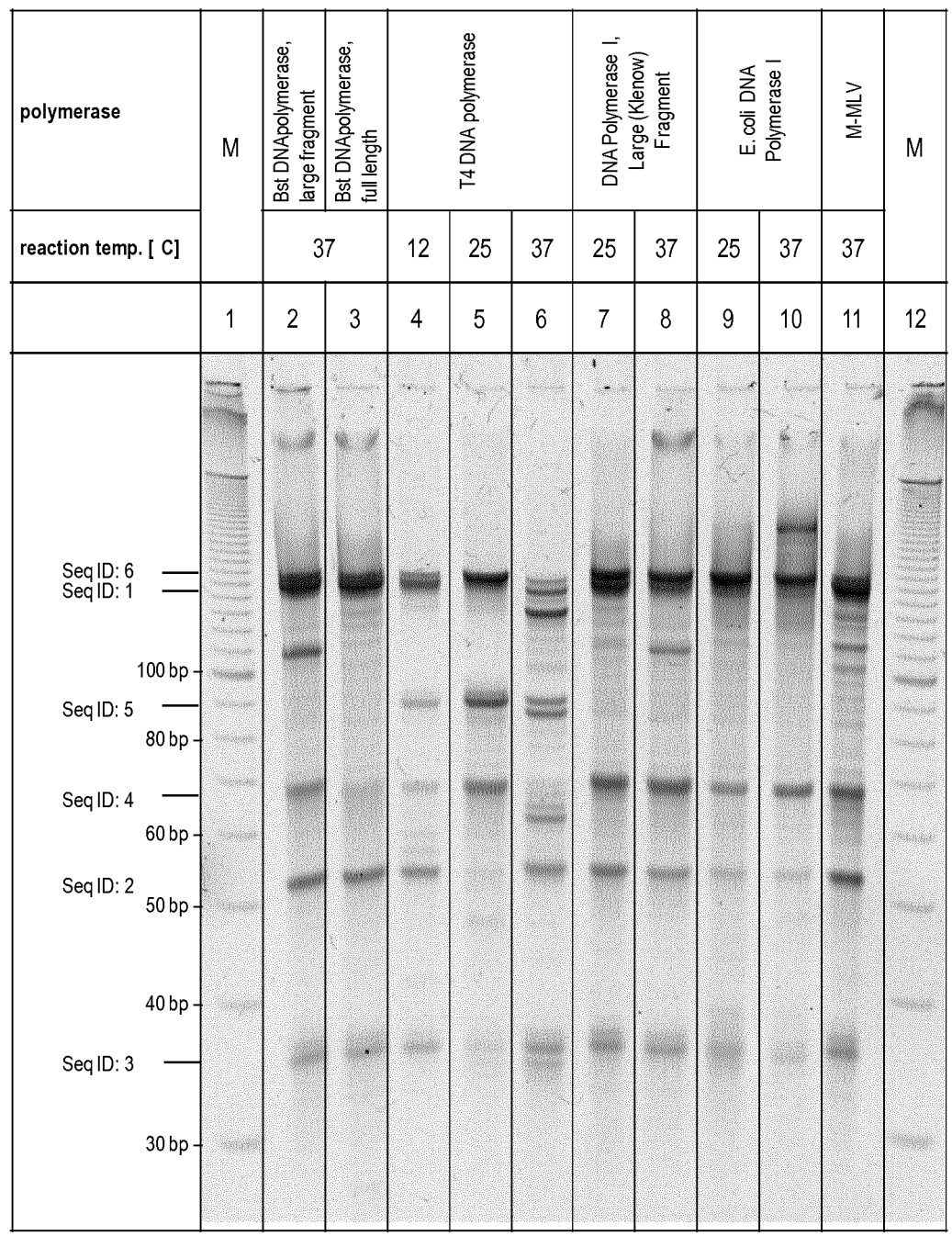

FIG. 4: Further comparison of polymerases with and without strand displacement activity at different reaction temperatures. 25° C. for T4 is more recommendable than 37° C. because at 37° C. the inherent exonuclease takes over the reaction.

Figure 5:
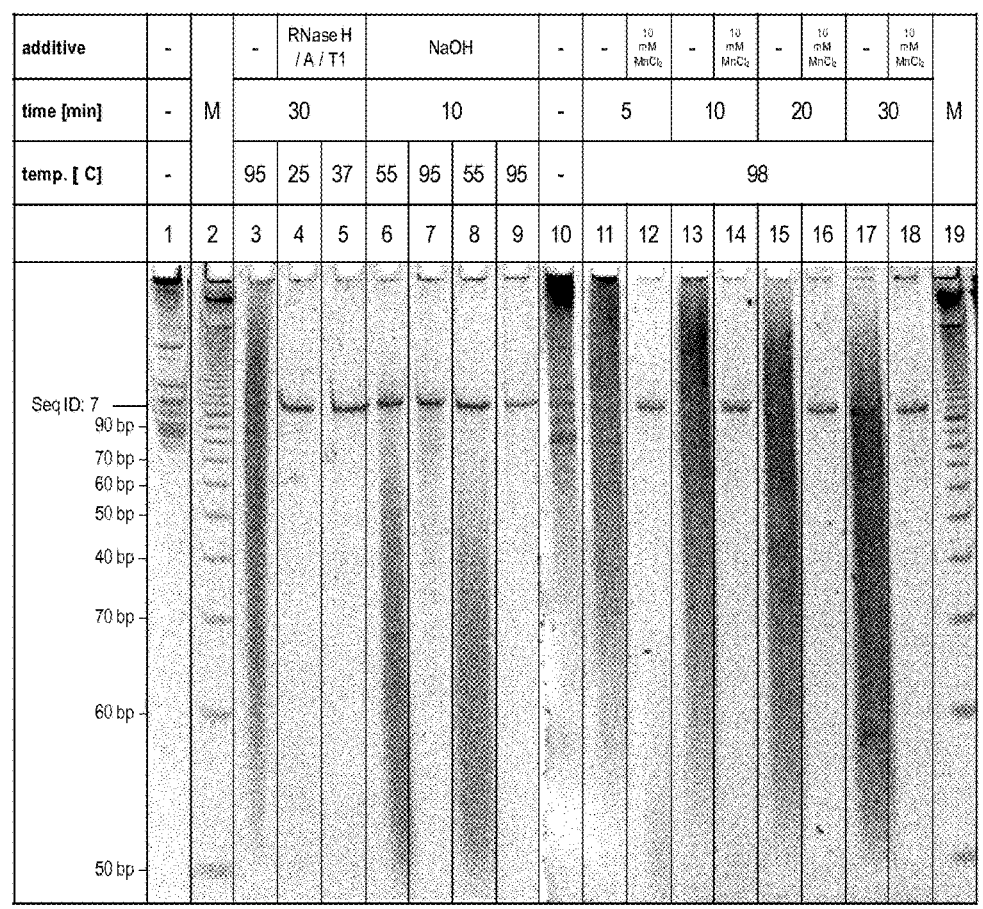

FIG. 5: Comparison of different RNA degradation methods with $MnCl_2$, elevated temperature only, NaOH treatment, or RNAses. Total RNA isolated from mouse liver was spiked with a 111 nt single stranded DNA (ssDNA) oligo (ID Seq ID: 7) see lane 1 and lane 10. Heat treatment in a standard RT-buffer 50 mM Tris-HCl (pH 8.3 at 25° C.), 75 mM KCl, 3 mM $MgCl_2$ and 10 mM DTT for 30 minutes at 95° C. and for 5 minutes at 98° C., 10 minutes at 98° C., 20 minutes at 98° C., and 30 minutes at 98° C., results in degradation of the RNA, but not a complete removal of the RNA. Incubation of the RNA/ssDNA mixture with RNase H/A/T1 mix for 30 minutes either at 25° C. or at 37° C. completely removes the RNA without degrading the single stranded DNA. Incubation at elevated temperatures for 10 minutes (55° C.) in the presence of 0.1 N NaOH degrades the RNA, although not completely. After 10 minutes 95° C. in 0.1 N NaOH the RNA is completely removed however also the ssDNA starts degrading (lanes 7-10). Addition of 10 mM $MnCl_2$ to the RNA/ssDNA/RT buffer mixture and heat treatment for 5, 10, 20 and 30 minutes at 98° C. results in complete degradation of the RNA without degrading ssDNA.

Figure 6:
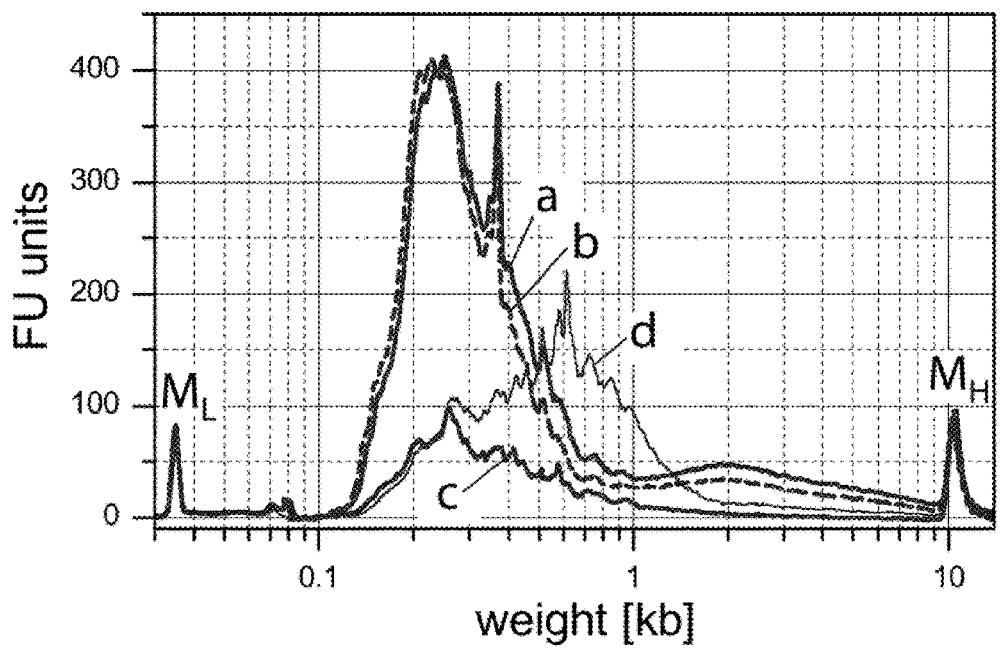

FIG. 6: Effect of the initial RNA fragmentation on library size and efficiency. a) and b) was fragmented in presence of 6 mM $MnCl_2$ and finally amplified for 14 PCR cycles, whereas c) and d) was fragmented in the presence of 4 mM $MnCl_2$ and required 2 more PCR cycles. All fragmentations proceeded for 3 min at 85° C.

Figure 7:
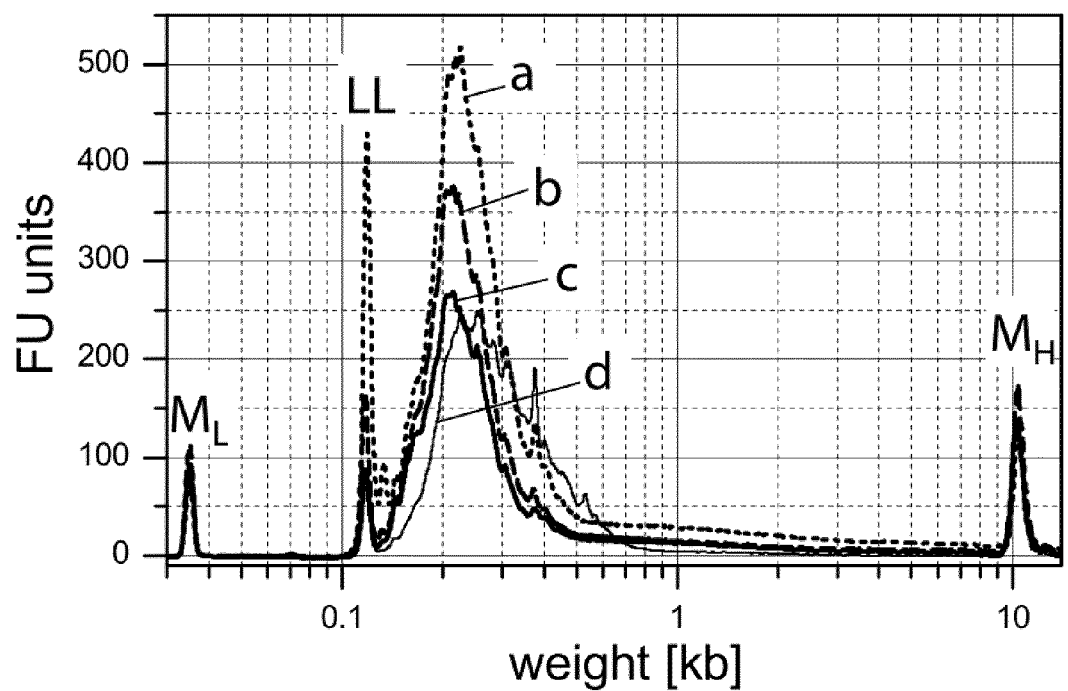

FIG. 7: Influence of the RT primer concentration and $2^{nd}$ strand synthesis primer concentration on the library size and yield. a) 50 nM anchored polydT (RT) primer (SEQ ID No: 8) and 1 µM $2^{nd}$ strand synthesis oligo+rc (SEQ ID No:9 and 10), b) 25 nM anchored polydT (RT) primer and 0.5 µM $2^{nd}$ strand synthesis oligo+rc, library 1:3 diluted before loading, c) 50 nM anchored polydT (RT) primer and 0.5 µM $2^{nd}$ strand synthesis oligo+rc, library 1:3 diluted before loading, d) 25 nM anchored polydT (RT) primer and 0.1 µM $2^{nd}$ strand synthesis oligo+rc.

Figure 8:
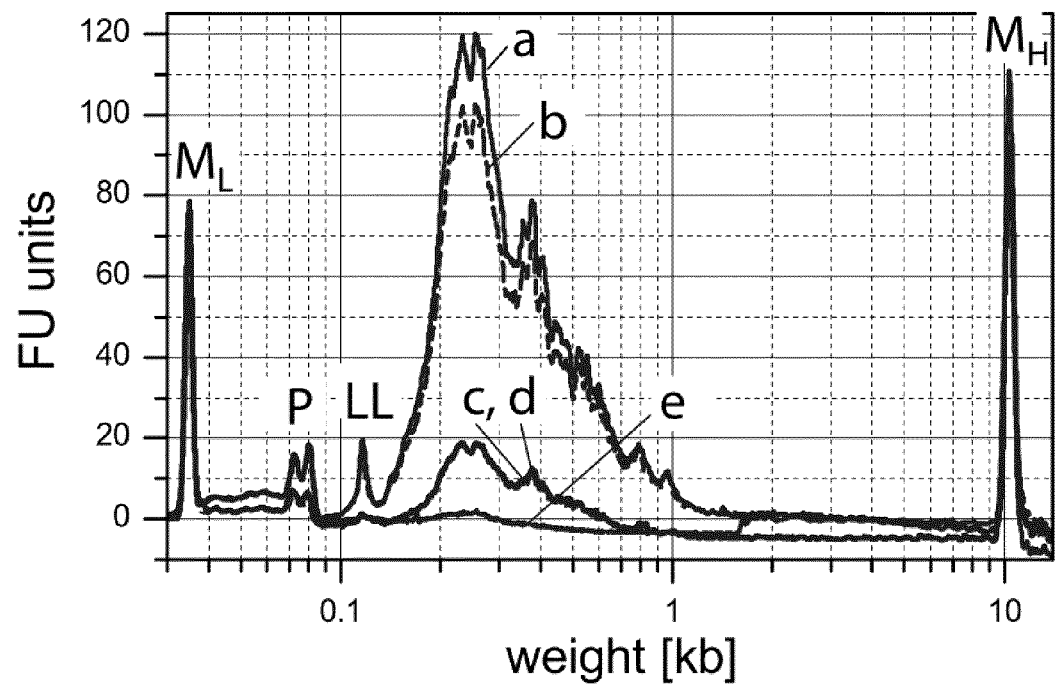

FIG. 8: Influence of the RNA degradation method on the quality of NGS libraries. The RNA has been degraded through a) 10 mM $MnCl_2$ for 10 min at 95° C., b) 5000 U RNAse H for 30 min at 37° C., c) buffer for the reverse transcription for 10 min at 95° C., d) 100 mM NaOH for 10 min at 95° C., and e) 200 mM $MnCl_2$. ML, low molecular weight marker; MH, high molecular weight marker; P, remaining primer; LL, linker-linker fragments.

Figure 9:
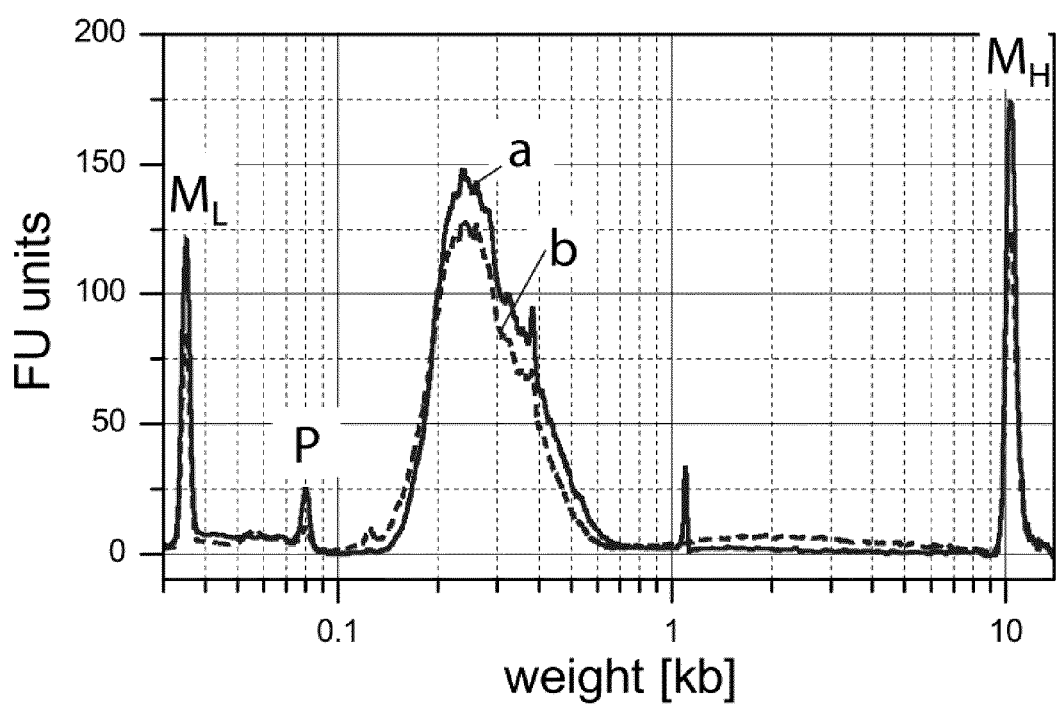

FIG. 9: Comparison between Silica column and SPRI purification after the 2nd strand synthesis. a) SPRI purification with hydroxyl-modified magnetic beads and a salt-PEG buffer, and b) silica column purification with a pH buffer system.

FIG. 10: Nucleotide sequences

EXAMPLES

Example 1:

3' terminal NGS library generation for an Illumina sequencing platform

In short, the principle library generation is carried out as described in FIG. 1. a) cDNA synthesis is initiated by priming to a known region or tag which is either present already (here Poly(A) of mRNA) or attached in a preceding reaction. P1 is complementary to said known region and furthermore contains a non complementary specific sequence at its 5' end serving as a universal tag. b) RNA is reverse transcribed into cDNA by an RNA dependent polymerase i.e. a reverse transcriptase. c) After cDNA synthesis the RNA template is hydrolyzed or degraded either by RNAses, pH changes (NaOH and heat), or divalent cations ($Mn^{2+}$, $Mg^{2+}$ and heat). d) Then, the single stranded cDNA is primed by multiple random primers, P(n), P(n+1), . . . , P(n+n), and e) a second strand is synthesized using a DNA dependent polymerase without strand displacement. The lack of strand displacement guarantees that only the most 3' fragment will contain both tags, one from the cDNA synthesis primer and the other one from the 2nd strand synthesis primer.

The individual reaction steps are described in more detail in the following.

The library generation starts with the first strand cDNA synthesis through reverse transcription where an oligodT primer containing one Illumina-compatible sequences at its 5' end is hybridized to the RNA after which reverse transcription takes place. For this purpose, for one individual library preparation 5 µl of RNA were mixed with 5 µl First Strand cDNA Synthesis Mix 1 containing all components necessary for a reverse transcription including an oligo dT primer without the enzyme in one well of a PCR plate, alternatively in one well of a 8-well strip or in any other thermocycler compatible tube. If a smaller volume of RNA is used RNAse-free water is added to gain a total volume of 10 µl. Then the solution well is mixed by pipetting and the PCR plate sealed. The seal is applied tightly. The plate is spun down so all liquid is collected at the bottom of the wells. Then the RNA/RT mixture is denatured for 3 min at 85° C. in a thermocycler and then cooled down to 37° C. to allow hybridization of the RT primer a). The plate is spun down to make sure all liquid is collected at the bottom of the wells before carefully removing the sealing foil.

Afterwards 10 µl of a reverse transcriptase dilution are mixed to each reaction by pipetting before the plate is sealed again. The liquid needs to be spun down and in step b) the plate is incubated at 37° C. for 15 minutes.

c) The RNA template is removed. During this step the RNA template is destroyed which is essential for efficient second strand synthesis. Before removing the sealing foil after the first strand synthesis reaction the plate is quickly spun down to ensure that all liquid is collected at the bottom of the wells. 5 µl of an RNA Removal Solution is directly added to the first strand synthesis reaction and mixed well and the plate resealed using a fresh foil. The plate must be incubated for 10 minutes at 95° C. before it is cooled down to 25° C., and spun down. Now, the sealing foil is removed carefully, 5 µl of Removal Solution 2 (which basically removes or neutralizes the component added with Removal Solution 1) are added and the solution is mixed well again.

d) During the following Second Strand Synthesis the library is converted to dsDNA. The Second strand synthesis is initiated by a random primer containing an Illumina-compatible linker sequence at its 5' end. A reverse complement prevents the linker sequence from taking part in the hybridization. At this stage it is recommend to taking the purification beads (SPRI beads) to room temperature to give them enough time to equilibrate. 15 µl Second Strand Synthesis Mix 1 (containing all the components necessary for a DNA dependent polymerization reaction) are added, mixed well by pipetting and the plate is sealed. Now, the plate is incubated for 1 min at 98° C. in a thermocycler and slowly cooled down to 25° C. by setting the ramp speed to 0.5° C. per second which corresponds at many thermocyclers to 10% of the maximal ramp speed. The reaction is incubated for 30 min at 25° C., quickly spun down before removing the sealing foil from the plate.

e) 5 µl of a DNA dependent polymerase dilution are added. The reaction is incubated at 25° C. for 15 minutes. Up to step e) the entire reaction has been carried out in one successively increasing volume. The reaction continues by entering the selection step f).

f) The double-stranded library which still contains undesired double strands which do not contain the P1 sequence is purified using magnetic beads. The purification beads (PB) should have been equilibrated for 30 min at room temperature before use. PB may have settled and must be properly resuspended before being added to the reaction. Afterwards a SPRI purification is carried out according to the manufacturer's (AMPure Beads; Agentcourt) instruction. Libraries are eluted in 20 µl water or 10 mM Tris, pH 8.0 and 17 µl of the clear supernatant with the library are transferred into a new clean PCR plate. Care must be taken to not transfer any beads into the new plate. The libraries can be stored at −20° C. for later amplification.

The most 3' fragments are isolated through PCR amplification. The library is also amplified to add the complete adapter sequences required for cluster generation on NGS machines and to generate sufficient material for quality control and the subsequent lane mixes. A standard PCR reaction using a thermostable DNA polymerase is carried out and afterwards the products are again purified by a final purification (SPPRI purification according to the manufacturer's instruction) in which the finished library is isolated from any remaining PCR components and where all the input DNA material which did not contain both sequence P1 and Pn is displaced in the overall representation through the relative dilution process of the PCR. Remanent sequences which do not contain both sequences P1 and Pn will not be able to generate clusters in the NGS process because the cluster generation uses a PCR amplification starting from single molecules only which contain both sequences. The final libraries are eluted in 20 µl of EB are added, and the beads resuspended properly in EB before incubating for 2 minutes at room temperature. The plate is placed onto a magnetic plate to collect the beads collect for 5 minutes or until the supernatant is completely clear. The supernatant is transferred into a fresh PCR plate. At this point, the libraries are finished and ready for quality control, pooling, cluster generation and further sequencing.

Example 2:

comparison of non-stopping polymerases with strand displacement activity (klenow) and stopping polymerases without strand displacement activity (T4 and T7) at different temperatures (FIGS. 2, 3 & 4)

Assay Description:

A schematic representation of the assay set up is shown and described in FIG. 2. Different polymerases with strand displacement, with and without ability to destroy the displaced stand and polymerases without strand displacement were evaluated using the assay described in FIG. 2. Briefly Seq ID: 1, Seq ID: 2 and Seq ID: 3 were hybridized in the corresponding buffer of the different polymerases. After hybridization polymerases were added (3 U T4 DNA polymerase, 10 U T7 DNA polymerase, or 5 U Klenow Fragment (3'-5' exo-), and the reaction was performed as indicated in FIG. 3 and FIG. 4. Reaction time was 10 minutes at the indicated temperature. Afterwards the reactions were purified via silica columns to remove buffer components and enzymes without any size selection. Samples were loaded onto a 10% PAA gel (mixed with loading dye and denatured for 2 minutes at 95° C.) and run at 100 V for 10 minutes and then at 180 V for 120 minutes at 58° C. Gels were stained with GYBR Gold.

In FIG. 3 the importance of a denatuation and slow annealing step (from 95° C. down to the reaction temperature with a slower ramp (takes 15 min) is demonstrated as for polymerases without strand displacement secondary structures in the template pose a significant obstacle. White filled arrows indicate partially displaced strand displacement stop products. Secondary structures of the single stranded template without the denaturation step are indicated with a black arrow. Klenow always shows strand displacement (especially at higher temperatures and here also a denaturation step to prevent secondary structures in the cDNA is not essential as the enzyme can dissolve those secondary structures with its inherent strand displacement (FIG. 2). FIG. 4 demonstrates the strand displacement of five different polymerases. The assay was performed as described above with the corresponding buffers, an initial denaturation step and at reaction temperatures as indicates in FIG. 4. Polymerases with strand displacement: 8 units Bst DNA polymerase, large fragment lane: 2; 5 units DNA polymerase I, Large (Klenow) Fragment, lane 7-8; and 200 units M-MLV, lane 11; and polymerases without strand displacement: lane 3, 3 units T4 DNA polymerase, lanes 4-6, or a polymerase that destroy the displaced strand such as 5 Units Bst DNA polymerase, full length, lane 3, 10 units E. coli DNA polymerase I, lane 9-10. Different reaction temperatures were checked: 12° C.: lane: 4; 25° C.: lanes: 5, 7, 9; 37° C.: lanes: 2-3, 6, 8, 10-11). T4 DNA polymerase contains an exonuclease activity that becomes prominent at 37° C. Degradation products of Seq ID: 1, Seq ID: 5, Seq ID: 2, and Seq ID: 3 are visible. With Bst DNA polymerase, large fragment, DNA polymerase I, Large (Klenow) Fragment and M-MlV there is a strand displacement and Seq ID 6 (full length product) is visible. Additionally a product larger than Seq ID: 5 is visible with those polymerases resulting from a partial strand displacement. With other strand displacing polymerases such Bst DNA polymerase, full length, (lane 3) and E. coli DNA polymerase I (lane 9-10) the displaced strand also gets destroy. T4 DNA polymerase does not contain strand displacement and Seq ID 5 is clearly visible. 25° C. for T4 is more recommendable than 37° C. because at 37° C. the inherent exonuclease takes over the reaction (FIG. 4).

Example 3:

RNA degradation with $MnCl_2$, elevated temperature only, NaOH treatment, or RNAses (FIG. 5) degradation of RNA also depends on the buffer conditions Total RNA isolated from mouse liver was spiked with a 111 nt single stranded DNA (ssDNA) oligo (ID Seq ID: 7) see lane 1 and lane 10. Total RNA is long hence only smaller RNA band are visible on the gel, the long RNA fragments remain in the slot. Upon fragmentation the longer RNA fragments become degraded and are visible as a smear on the polyacrylamide gel.

Heat treatment in a standard RT-buffer 50 mM Tris-HCl (pH 8.3 at 25° C.), 75 mM KCl, 3 mM $MgCl_2$ and 10 mM DTT for 30 minutes at 95° C. and for 5 minutes at 98° C., 10 minutes at 98° C., 20 minutes at 98° C., and 30 minutes at 98° C., results in degradation of the RNA, but not a complete removal of the RNA. Incubation of the RNA/ ssDNA mixture with RNase H/A/T1 mix for 30 minutes either at 25° C. or at 37° C. completely removes the RNA without degrading the single stranded DNA. Incubation at elevated temperatures for 10 minutes (55° C.) in the presence of 0.1 N NaOH degrades the RNA, although not completely. After 10 minutes 95° C. in 0.1 N NaOH the RNA is completely removed however also the ssDNA starts degrading (lanes 7-10). Addition of 10 mM $MnCl_2$ to the RNA/ssDNA/RT buffer mixture and heat treatment for 5, 10, 20 and 30 minutes at 98° C. results in complete degradation of the RNA without degrading ssDNA. Samples were loaded onto a 10% PAA gel without purification (mixed with loading dye and denatured for 2 minutes at 95° C.) and run at 100 V for 10 minutes and then at 180 V for 70 minutes at 58° C. Gels were stained with GYBR Gold.

Example 4:

Influence of the RNA degradation method on the quality of NGS libraries synthesized with a polymerase without strand displacement (FIG. 6)

500 ng total RNA were mixed with Seq ID: 8 (final concentration in 20 µl: 25 nM) and heated to 85° C. for 3 minutes in a volume of 10 µl containing 4 µl of 5×RT buffer. After cooling to 37° C. 1 µl 1 mM dNTPs, 200 units M-MLV were added an incubated for 15 minutes at 37° C. Subsequent RNA hydrolysis differs as shown in FIG. 6. Biotin-Streptavidin fishing in RT reaction buffer was carried out for 20 min (on shaker at 1250 rpm at 25° C.) using 5 µg straptavidin beads from NEB. Beads were washed 2× with wash buffer, and samples were released from the beads by heating to 80° C. for minutes in 10 µl $MB-H_2O$. Beads were collected using a magnet and the clear supernatant was transferred to a different tube were second strand cDNA synthesis was carried out using 3 units T4 DNA polymerase Seq ID: 9 and 10 (final concentration in 20 µl 0.1 µM), 8% PEG, 10 mM $MgCl_2$ and 0.5 mM dNTPs in a total volume of 20 µl. Before adding the polymerase a denaturation step was included 98° C., 1 minute and a slow annealing (ramp down to 25° C. within 15 minutes). Samples were then silica purified according to the SENSE user guide (section purification after second strand synthesis) and eluted in 25 µl 10 mM Tris pH 8. 10 µl of the purified product and were then amplified for 18 cycles according to the SENSE mRNA Seq PCR using Seq ID: 11 and 12 as PCR primers. Samples were then silica purified according to the SENSE user guide (section purification after second strand synthesis) and eluted in 15 µl 10 mM Tris pH8. 1 µl purified PCR product loaded on High-sensitivity DNA-Chip (Agilent) according to manufacturer's instructions RNAses and $MnCl_2$ degradation of the RNA results in a much higher yield than NaOH hydrolysis which either damages the cDNA or results in base modifications that render the cDNA unamplifyable.

Example 5:

The initial fragmentation of the RNA in the RT buffer determines the library size and efficiency of the protocol (FIG. 6)

The volume in which the RNA is denatured also has an influence on the $MgCl_2$ concentration that is present during the denaturation and this also determines how long the cDNA will be that is generated from the slightly fragmented RNA 500 ng total RNA were mixed with Seq ID: 8 (final concentration in 20 µl: 25 nM) and heated to 85° C. for 3 minutes in a volume of 10 µl (a and b) or 15 µl (c and d) containing 4 µl of 5×RT buffer. After cooling to 37° C. 1 µl 1 mM dNTPs, 200 units M-MLV were added an incubated for 15 minutes at 37° C. RNA was hydrolysed in the presence of 10 mM $MnCl_2$ by heating to 98° C. for 10 minutes. Afterwards 10 mM EDTA were added. Second strand synthesis was performed by adding the second strand synthesis components to the reaction resulting in a final concentration of 10 mM $MgCl_2$, 0.5 mM dNTPs, 8% PEG, SEQ ID: 9 and 10 each 100 nM final concentration and 3 units T4 DNA polymerase in a total volume of 40 µl. Again the polymerase was added after heating to 98° C. for 1 minute and a slow annealing (ramp down to 25° C. within 15 minutes. Purification, PCR amplification and subsequent PCR purification and the bioanalyzer run was carries out as described in example 4.

Example 6:

adjusting library size and yield by RT primer concentration and 2nd strand synthesis oligo concentration (FIG. 7)

All libraries 17 cycles. All rxn conditions acc. to example 5 varying concentrations of a) 50 nM Seq ID: 8 during the reverse transcription (RT) step and 0.1 µM Seq ID: 9 and 10, in second strand synthesis (SSS) b) 25 nM Seq ID: 8 during RT and 0.5 µM Seq ID: 9 and 10 during SSS, library 1:3 diluted before loading, c) 50 nM Seq ID: 8 during RT and 0.5 µM Seq ID: 9 and 10 during SSS, library 1:3 diluted before loading, d) 25 nM Seq ID:8 during RT and 0.1 µM Seq ID: 9 and 10 during SSS.

Example 7:

Silica vs. SPRI purification (FIG. 8)

All steps as described in example 6 (c) but with different purification. Silica purifications were done as decrobed in example 5 and SPRI purification with hydroxyl-modified magnetic beads and a salt-PEG buffer was performed according to the manufacturer's (AMPure XP beads from Agentcourt) instructions.

REFERENCES

Costa V, et al. (2010) J Biomed Biotech 7(7): 1299-20.
Derti A, et al. (2012) Genome Res. 22(6): 1173-83.
Fox-Walsh K, et al. (2011) Genomics. 98(4): 266-71.
Hawkins T L, et. al. (1995) Nucleic Acids Res. 23: 4742-4743.
Mainul Hoque et al., (2012) Nature Methods 10(2): 133-139.
Shepard P J, et al. (2011) RNA 17: 761-772.

Wendl M C and Wilson R K (2009) BMC Genomics 10: article 485.
Wilkening S, et al. (2013) Nucleic Acids Res. 41(5): e65.
WO 98/044151
WO 02/059357
U.S. Pat. No. 5,705,628
US 2011/0160078US 6406891 B1
EP 1371726 A1
WO 2013/038010 A2

The invention claimed is:

1. A method for generating a nucleic acid product from a template RNA molecule, comprising after having obtained a template RNA:
   (a) annealing a first oligonucleotide primer at a preselected nucleic acid region of the template RNA;
   (b) elongating the first oligonucleotide primer in a template specific manner thereby obtaining a first elongated strand;
   (c) removing the RNA template;
   (d) annealing more than one further oligonucleotide primers to the first elongated strand;
   (e) elongating the more than one further oligonucleotide primers:
      i) in a template specific manner without displacement of primers annealed to the first elongated strand, wherein the primers have an increased melting temperature as compared to natural oligonucleotides, and/or a polymerase without displacement activity is used for said elongating; or
      ii) with a polymerase that destroys a displaced strand, thereby generating further elongation products; and
   (f) isolating and/or amplifying from said further elongation products, an elongation product that comprises a nucleic acid portion complementary to the first oligonucleotide primer.

2. The method of claim 1, wherein the preselected nucleic acid region is a 3' terminal nucleic acid region.

3. The method of claim 2, wherein the method further comprises the step of attaching a 3' polynucleotide tail to the 3' end of the template RNA, wherein said preselected 3' terminal nucleic acid region comprises said 3' polynucleotide tail.

4. The method of claim 2, wherein the 3' terminal nucleic acid region comprises a poly-A tail.

5. The method of claim 1, wherein the first oligonucleotide primer and/or further oligonucleotide primers is/are DNA.

6. The method of claim 1, wherein the first oligonucleotide primer and/or further oligonucleotide primers contain a non-annealing sequence tag.

7. The method of claim 6, wherein the non-annealing sequence tag contains a barcode.

8. The method of claim 7, wherein the barcode is a random barcode.

9. The method of claim 6, further comprising binding amplification primers to the non-annealing sequence tag.

10. The method of claim 1, wherein (b) the elongating the first oligonucleotide primer in a template specific manner is by reverse transcription and the first elongated strand is a DNA strand.

11. The method of claim 1, wherein (c) removing the RNA template comprises enzymatic RNA digestion, alkaline degradation, or heating in the presence of divalent cations.

12. The method of claim 1, wherein the more than one further oligonucleotide primer comprises random primers and/or at least 10 different primers.

13. The method of claim 1, wherein the preselected nucleic acid region is present on one or multiple template RNAs of interest.

14. The method of claim 1, wherein in (d) the more than one further oligonucleotide primers each bind to different sequences on the first elongated strand.

15. The method of claim 1, wherein (e) elongating the more than one further oligonucleotide primer in a template specific manner is performed with a polymerase lacking strand displacement activity, and/or using primers having resistance to strand displacement by a polymerase, and/or in the presence of a crowding agent.

16. The method of claim 15, wherein the polymerase lacking strand displacement activity is a T7, T4 or Q5 DNA polymerase, wherein the primers having resistance to strand displacement by a polymerase have nucleotides with LNA or 2'fluor modifications, and/or wherein the crowding agent is PEG.

17. The method of claim 1, wherein the template RNA prior to first primer annealing is fragmented.

18. The method of claim 1, wherein steps (a) to (e) are performed in one container or without fluid removal.

19. The method of claim 1, further comprising a step of purifying the elongation products of step (e).

20. The method of claim 1, comprising performing a PCR on the further elongation products using a primer specific for sequence tags of said elongation products.

21. The method of claim 20, wherein at least one primer of the PCR comprises a further sequence tag.

22. The method of claim 1, further comprising using a kit to perform the steps (a) to (f), wherein the kit comprises a reverse transcriptase, dNTPs, cofactors or salts of metal ions required by a polymerase, the first oligonucleotide primer, the more than one further oligonucleotide primers, a DNA polymerase without strand displacement activity or a DNA polymerase that destroys a displaced strand.

23. The method of claim 22, wherein the kit further comprises a RNA degradation agent and/or a crowding agent.

24. The method of claim 23, wherein the crowding agent is PEG.

25. The method of claim 22, wherein a cofactor or salt of metal ions required by the polymerase is Mg2+.

26. The method of claim 22, wherein the DNA polymerase without strand displacement activity is T7, Q5 or T4 DNA polymerase.

27. The method of claim 26, wherein the kit further comprises a RNA degradation agent and/or a crowding agent.

28. The method of claim 27, wherein the crowding agent is PEG.

29. The method of claim 26, wherein the cofactors or salts of metal ions required by the polymerase are Mg2+.

* * * * *

SEQUENCE LISTING

```
<160> NUMBER OF SEQ ID NOS: 12

<210> SEQ ID NO 1
<211> LENGTH: 145
<212> TYPE: DNA
<213> ORGANISM: Artificial Sequence
<220> FEATURE:
<223> OTHER INFORMATION: Synthetic Polynucleotide

<400> SEQUENCE: 1
actgtaaaac gacggccagt atagttcgct cggtgaccct ggtctttctg gtgcttgtct     60
cactgaccgg cctgtatgct atccagagtg agtgcctctt gtcaagaaca tatagatagg    120
ctccgttgct aatctgaagg tcgaa                                          145

<210> SEQ ID NO 2
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 2
gtccagctac ctaggtcatg tactacggag cctatctata tgttcttgac a              51

<210> SEQ ID NO 3
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 3
cagtgagaca agcaccagaa agaccagggt caccg                                35

<210> SEQ ID NO 4
<211> LENGTH: 65
<212> TYPE: DNA
<213> ORGANISM: Artificial Sequence
<220> FEATURE:
<223> OTHER INFORMATION: Synthetic Polynucleotide

<400> SEQUENCE: 4
cagtgagaca agcaccagaa agaccagggt caccgagcga actatactgg ccgtcgtttt     60
acagt                                                                 65

<210> SEQ ID NO 5
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 5
gtccagctac ctaggtcatg tactacggag cctatctata tgttcttgac aagaggcact     60
cactctggat agcatacagg ccggt                                           85

<210> SEQ ID NO 6
```

-continued

```
<211> LENGTH: 150
<212> TYPE: DNA
<213> ORGANISM: Artificial Sequence
<220> FEATURE:
<223> OTHER INFORMATION: Synthetic Polynucleotide

<400> SEQUENCE: 6
gtccagctac ctaggtcatg tactacggag cctatctata tgttcttgac aagaggcact      60
cactctggat agcatacagg ccggtcagtg agacaagcac cagaaagacc agggtcaccg     120
agcgaactat actggccgtc gttttacagt                                      150

<210> SEQ ID NO 7
<211> LENGTH: 111
<212> TYPE: DNA
<213> ORGANISM: Artificial Sequence
<220> FEATURE:
<223> OTHER INFORMATION: Synthetic Polynucleotide

<400> SEQUENCE: 7
gttgtcacca gcatccctag acccgtacag tgcccactcc ccttcccagt ttccgactgt      60
ccccggcctc ctgcggccca ttccaaaaaa aaaaaaaaaa aaaaaaaaaa a              111

<210> SEQ ID NO 8
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 8
tccctacacg acgctcttcc gatctttttt ttttttttt tttv                        44

<210> SEQ ID NO 9
<211> LENGTH: 24
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (24)..(24)
<223> OTHER INFORMATION: inverted dt

<400> SEQUENCE: 9
agatcggaag agcacacgtc tgat                                             24

<210> SEQ ID NO 10
<211> LENGTH: 36
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (25)..(36)
<223> OTHER INFORMATION: n is a, c, g, or t

<400> SEQUENCE: 10
ttcagacgtg tgctcttccg atctnnnnnn nnnnnn                                36

<210> SEQ ID NO 11
<211> LENGTH: 58
<212> TYPE: DNA
<213> ORGANISM: Artificial Sequence
<220> FEATURE:
<223> OTHER INFORMATION: Synthetic Polynucleotide
```

```
<400> SEQUENCE: 11
aatgatacgg cgaccaccga gatctacact ctttccctac acgacgctct tccgatct        58

<210> SEQ ID NO 12
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 12
caagcagaag acggcatacg agatgtgact ggagttcaga cgtgtgctct tccgatct        58
```